(12) United States Patent
Bystrom et al.

(10) Patent No.: US 10,648,989 B2
(45) Date of Patent: May 12, 2020

(54) QUANTITATION OF INSULIN-LIKE GROWTH FACTOR-I AND INSULIN-LIKE GROWTH FACTOR-II WITH HIGH-RESOLUTION MASS SPECTROMETRY

(71) Applicant: Quest Diagnostics Investments Incorporated, Wilmington, DE (US)

(72) Inventors: Cory Bystrom, Los Angeles, CA (US); Shijun Sheng, Las Flores, CA (US); Nigel Clarke, Vista, CA (US); Richard E. Reitz, Las Vegas, NV (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 15/602,764

(22) Filed: May 23, 2017

(65) Prior Publication Data

US 2018/0128841 A1    May 10, 2018

Related U.S. Application Data

(63) Continuation of application No. 12/939,996, filed on Nov. 4, 2010, now abandoned.

(60) Provisional application No. 61/408,535, filed on Oct. 29, 2010, provisional application No. 61/258,560, filed on Nov. 5, 2009.

(51) Int. Cl.
*G01N 33/74*     (2006.01)
*G01N 33/68*     (2006.01)

(52) U.S. Cl.
CPC ......... *G01N 33/74* (2013.01); *G01N 33/6848* (2013.01)

(58) Field of Classification Search
CPC .......................... G01N 33/74; G01N 33/6848
See application file for complete search history.

(56) References Cited

U.S. PATENT DOCUMENTS

| | | | |
|---|---|---|---|
| 5,772,874 A | 6/1998 | Quinn et al. |
| 5,795,469 A | 8/1998 | Quinn et al. |
| 5,851,907 A | 12/1998 | Mohan et al. |
| 5,919,368 A | 7/1999 | Quinn et al. |
| 5,968,367 A | 10/1999 | Quinn et al. |
| 6,107,623 A | 8/2000 | Bateman et al. |
| 6,124,137 A | 9/2000 | Hutchens et al. |
| 6,204,500 B1 | 3/2001 | Whitehouse et al. |
| 6,268,144 B1 | 7/2001 | Koester |
| 6,995,364 B2 | 2/2006 | Makarov et al. |

(Continued)

OTHER PUBLICATIONS

Bantscheff M., et al., "Robust and Sensitive iTRAQ Quantification on an LTQ Orbitrap Mass Spectrometer," Molecular and Cellular Proteomics, 2008, vol. 7 (9), pp. 1702-1713.

(Continued)

*Primary Examiner* — Lore R Jarrett
(74) *Attorney, Agent, or Firm* — Quest Diagnostics, Inc.

(57) ABSTRACT

Methods are provided for determining the amount of an IGF-I and/or IGF-II protein in a sample using high resolution/high accuracy mass spectrometry. The methods generally comprise enriching an IGF-I and/or IGF-II protein in a sample, ionizing an IGF-I and/or IGF-II protein from the sample to generate IGF-I and/or IGF-II protein ions, and determining the amount of IGF-I and/or IGF-II protein ions with high resolution/high accuracy mass spectrometry.

11 Claims, 23 Drawing Sheets

(56) References Cited

U.S. PATENT DOCUMENTS

| | | | | |
|---|---|---|---|---|
| 10,436,803 | B2* | 10/2019 | Chen | G01N 33/49 |
| 2004/0232327 | A1* | 11/2004 | Bateman | H01J 49/401 |
| | | | | 250/288 |
| 2008/0118932 | A1 | 5/2008 | Toler et al. | |
| 2008/0296486 | A1* | 12/2008 | Blanksby | H01J 49/0045 |
| | | | | 250/282 |
| 2009/0054320 | A1 | 2/2009 | Buchanan et al. | |

OTHER PUBLICATIONS

Bayne S.J., et al., "Confirming the Primary Structures of Insulin-Like Growth Factors 1 and 2 Isolated From Porcine Plasma Using Mass Analysis," Peptide Research, 1990, vol. 3 (6), pp. 271-273.
Bayne S.J., et al., "Primary Sequences of Insulin-Like Growth Factors 1 and 2 Isolated from Porcine Plasma," Journal of Chromatography, 1991, vol. 562 (1-2), pp. 391-402.
Bobin S., et al., "Approach to the Determination of Insulin-Like-Growth-Factor-I (IGF-I) Concentration in Plasma by High-Performance Liquid Chromatography-Ion Trap Mass Spectrometry: Use of a Deconvolution Algorithm for the Quantification of Multiprotonated Molecules in Electrospray Ionization," Analyst, 2001, vol. 126 (11), pp. 1996-2001.
Bredehoft M., et al., "Quantification of Human Insulin-Like Growth Factor-1 and Qualitative Detection of Its Analogues in Plasma Using Liquid Chromatography/Electrospray Ionisation Tandem Mass Spectrometry," Rapid Communications in Mass Spectrometry, 2008, vol. 22 (4), pp. 477-485.
Bystom C., et al., "Clinical Utility of Insulin-Like Growth Factor 1 and 2; Determination by High Resolution Mass Spectrometry," PLOS One, 2012, vol. 7 (9), pp. e43457.
Bystrome C.E., et al., "Narrow Mass Extraction of Time-of-Flight Data for Quantitative Analysis of Proteins: Determination of Insulin-Like Growth Factor-1," Analytical Chemistry, 2011, vol. 83 (23), pp. 9005-9010.
De Kock S.S., et al., "Growth Hormone Abuse in the Horse: Preliminary Assessment of a Mass Spectrometric Procedure for IGF-1 Identification and Quantitation," Rapid Communications in Mass Spectrometry, 2001, vol. 15 (14), pp. 1191-1197.
Examiner's Answer to Appeal Brief dated Mar. 3, 2016 for U.S. Appl. No. 12/939,996, filed Nov. 4, 2010.
Extended European Search Report for Application No. 10829122.0, dated Feb. 25, 2013.
Extended European Search Report for Application No. EP16174510.4, dated Aug. 16, 2016, 13 pages.
Final Office Action dated Nov. 14, 2013 for U.S. Appl. No. 12/939,996, filed Nov. 4, 2010.
Final Office Action dated Oct. 20, 2014 for U.S. Appl. No. 12/939,996, filed Nov. 4, 2010.
Hampton B., et al., "Purification and Characterization of Insulin-Like Growth Factor II Variant from Human Plasma," The Journal of Biological Chemistry, 1989, vol. 264 (32), pp. 19155-19160.
Hardware Manual: API 4000™ LC/MS/MS System Part No. 5005565 A Apr. 2010.file:///C:/Users/ygakh/Downloads/4000-api-hardware-guide 20(1).pdf.
International Preliminary Report on Patentability for Application No. PCT/US2010/055518, dated May 18, 2012.
International Search Report and Written Opinion for Application No. PCT/US2010/055518, dated Jan. 14, 2011.
Jespersen S., et al., "Characterization of O-Glycosylated Precursors of Insulin-like Growth Factor II by Matrix-Assisted Laser Desorption/Ionization Mass Spectrometry," Journal of Mass Spectrometry, 1996, vol. 31 (8), pp. 893-900.
Kirsch S., et al., "Development of an Absolute Quantification Method Targeting Growth Hormone Biomarkers Using Liquid Chromatography Coupled to Isotope Dilution Mass Spectrometry," Journal of Chromatography, 2007, vol. 1153 (1-2), pp. 300-306.
Le-Breton M.H., et al., "Direct Determination of Recombinant Bovine Somatotropin in Plasma from a Treated Goat by Liquid Chromatography/High-Resolution Mass Spectrometry," Rapid Communications in Mass Spectrometry, 2008, vol. 22 (20), pp. 3130-3136.
Mass Accuracy and Mass Resolution in TOF MS, by Agilent Technologies [Online], 2000. Retrieved from the Internet.
Merchant M., et al., "Recent Advancements in Surface-Enhanced Laser Desorption/Ionization—Time of Flight-Mass Spectrometry," Electrophoresis, 2000, vol. 21 (6), pp. 1164-1167.
Nelson R.E., et al., "Quantitative Mass Spectrometric Immunoassay of Insulin like Growth Factor 1," Journal of Proteome Research, 2004, vol. 3 (4), pp. 851-855.
Non-Final Office Action and Amendment After Final or Under 37CFR 1.312, Initialed by the Examiner dated Apr. 28, 2014 for U.S. Appl. No. 12/939,996, filed Nov. 4, 2010.
Non-Final Office Action dated Mar. 19, 2013 for U.S. Appl. No. 12/939,996, filed Nov. 4, 2010.
Non-Final Office Action dated Jan. 22, 2016 for U.S. Appl. No. 14/063,956, filed Oct. 25, 2013.
Olsen J.V., et al., "Higher-Energy C-Trap Dissociation for Peptide Modification Analysis," Nature Methods, 2007, vol. 4 (9), pp. 709-712.
Polson C., et al., "Optimization of Protein Precipitation Based Upon Effectiveness of Protein Removal and Ionization Effect in Liquid Chromatography—Tandem Mass Spectrometry," Journal of Chromatography B, 2003, vol. 785 (2), pp. 263-275.
Popot M.A., et al., "Determination of IGF-I in Horse Plasma by LC Electrospray Ionization Mass Spectrometry," Analytical and Bioanalytical Chemistry, 2008, vol. 390 (7), pp. 1843-1852.
Popot M.A., et al., "High Performance Liquid Chromatography-Ion Trap Mass Spectrometry for the Determination of Insulin-Like Growth Factor-I in Horse Plasma," Chromatographia, 2001, vol. 54, pp. 737-741.
Rousu T., et al., "Comparison of Triple Quadrupole, Hybrid Linear Ion Trap Triple Quadrupole, Time-of-Flight and LTQ-Orbitrap Mass Spectrometers in Drug Discovery Phase Metabolite Screening and Identification in Vitro—Amitnptyline and Verapamil as Model Compounds," Rapid Communications in Mass Spectrometry, 2010, vol. 24 (7), pp. 939-957.
Russell D.H., et al., "High Resolution Mass Spectrometry and Accurate Mass Measurements with Emphasis on the Characterization of Peptides and Proteins by Matrix assisted Laser Desorption Ionization Time of flight Mass Spectrometry", Journal of Mass Spectrometry, Wiley, Chichester, GB, vol. 32 (3), Jan. 1, 1997 (Jan. 1, 1997), pp. 263-276.
Schenk S., et al., "A High Confidence, Manually Validated Human Blood Plasma Protein Reference Set," BMC Medical Geonomics, 2008, vol. 1, pp. 41.
Scigelova M., et al., "Orbitrap Mass Analyzer—Overview and Applications in Proteomics," PractProteo, 2006, vol. 1 (2), pp. 16-21.
Significant Figures and Errors: courses.chem.psu.edu/chem110h/errors.pdf.
Smith M.C., et al., "Structure and Activity Dependence of Recombinant Human Insulin-Like Growth Factor II on Disulfide Bond Pairing," The Journal of Biological Chemistry, 1989, vol. 264 (16), pp. 9314-9321.
Supplementary European Search Report for Application No. EP10829122, dated Feb. 25, 2013, 8 pages.
The New Agilent 6530 Accurate-Mass Quadrupole TOF LC/MS System, Agilent Measurement Journal, Issue six, 2008.
Thevis M., et al., "Mass Spectrometric Determination of Insulins and Their Degradation Products in Sports Drug Testing," Mass Spectrometry Reviews, 2008, vol. 27 (1), pp. 35-50.
Thomas A., et al., "Determination of IGF-1 and IGF-2, Their Degradation Products and Synthetic Analogues in Urine by LC-MS/MS," Analyst, 2011, vol. 136 (5), pp. 1003-1012.
Thomas A., et al., "Mass Spectrometric Determination of Gonadotrophin-Releasing Hormone (Gnrh) in Human Urine for Doping Control Purposes by Means of LC-ESI-MS/MS," Journal of Mass Spectrometry, 2008, vol. 43 (7), pp. 908-915.
TOF MS Resolution and Mass Measurement Accuracy, Washington University of St. Lewis, School of Medicine [Online], 2013. Retrieved from the Internet.

(56) References Cited

OTHER PUBLICATIONS

Wadensten H., et al., "Purification and Characterization of Recombinant Human Insulin-Like Growth Factor II (IGF-II) Expressed as a Secreted Fusion Protein in *Escherichia coli*," Biotechnology and Applied Biochemistry, 1991, vol. 13 (3), pp. 412-421.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US10/55518, dated Jan. 14, 2011, 6 Pages.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography—Tandem Mass Spectrometry," Journal of Chromatography A, 1999, vol. 854, pp. 23-35.

Extended European Search Report for Application No. EP18168369.9, dated Jun. 28, 2018, 13 pages.

Kiefer P., et al., "Quantitative Metabolome Analysis Using Liquid Chromatography-High-Resolution Mass Spectrometry," Analytical Biochemistry, Nov. 2008, vol. 382 (2), pp. 94-100.

Mann M., et al., "Precision Proteomics: The Case for High Resolution and High Mass Accuracy," Proceedings of the National Academy of Sciences of the United States of America, Nov. 2008, vol. 105 (47), pp. 18132-18138.

\* cited by examiner

QUANTITATION OF INSULIN-LIKE GROWTH FACTOR-I AND INSULIN-LIKE GROWTH FACTOR-II WITH HIGH-RESOLUTION MASS SPECTROMETRY

CROSS-REFERENCE TO RELATED PATENT APPLICATIONS

This application is a continuation application of U.S. non-provisional application Ser. No. 12/939,996, filed Nov. 4, 2010, which claims priority to U.S. Provisional Application Ser. No. 61/258,560, filed Nov. 5, 2009, and U.S. Provisional Application Ser. No. 61/408,535, filed Oct. 29, 2010, which are incorporated herein by reference in their entirety including all figures and tables.

FIELD OF THE INVENTION

The invention relates to the quantitative analysis of large proteins using mass spectrometry.

BACKGROUND OF THE INVENTION

IGF-I is a hormone with a molecular structure similar to insulin. It is a peptide produced by the liver and contains 70 amino acids in a single chain with three intramolecular disulfide bridges. IGF-I has a molecular weight of about 7,649 Da, and is highly protein bound in serum. Production is stimulated by growth hormone and can be retarded by undernutrition, growth hormone insensitivity, lack of growth hormone receptors, or failure of a downstream signaling pathway. IGF-I plays an important role in childhood growth and continues to have anabolic effects in adults.

Insulin-like growth factor II (IGF-II) is also a hormone with a molecular structure similar to insulin. It is a single chain peptide that contains 67 amino acids. IGF-II has a molecular weight of about 7,505 Da, and is highly protein bound in serum. IGF-II is used as an adjunct to insulin-like growth factor I (IGF-I) in clinical evaluation of growth hormone-related disorders. IGF-II plays a role primarily in fetal growth and development by interplaying with IGF-I and different cell surface receptors and circulating binding proteins to modulate tissue growth. IGF-II levels are reduced in children and adults as a result of growth hormone deficiency or malnutrition. Increased IGF-II serum levels may be observed in acromegaly or with exogenous administration of IGF-I. Thus, measurement of circulating IGF-II levels (i.e. in plasma/serum) is an important tool in management of several growth hormone-related disorders. In addition, measurement of circulating IGF-II is also a valuable tool in various epidemiological research areas and clinical trials.

IGF-I and IGF-II have proven to be particularly challenging to quantitatively analyze with a "bottom up" approach (i.e., enzymatic digestion and quantitation of one or more of the resulting peptides). For example, de Kock, et al. reported that typical trypsin, chymotrypsin, and pepsin digestion methods result in low digestion yield and non-specific enzyme cleavage. de Kock, et al., Rapid Commun. Mass Spectrom., 2001, 15:1191-97. de Kock, et al. suggested that the unsatisfactory digestion results were likely due to steric restriction of the proteolytic enzymes by IGF-I's three disulfide bonds. Id.

Efforts have been made to develop methods to analyze IGF-I and IGF-II, including by a variety of mass spectrometric techniques. For example, analysis of IGF-I has been reported using LC-ion trap MS with single ion monitoring (SIM). See, e.g., Id.; Bobin, et al., Analyst, 2001, 126:1996-2001; and Popot, et al., Chromatographia, 2001, 54:737-741 (Popot I). These references disclose LC-ESI-ion trap MS of intact IGF-I at charge states ranging from 4+ to 9+ in SIM mode. More recently, LC-MS/MS techniques using multiple reaction monitoring (MRM) have been disclosed. Popot II reports quantitative analysis of IGF-I at charge states ranging from 4+ to 9+ using LC-ion trap MS with SIM, followed by qualitative confirmation of the analyte with LC-ion trap MS/MS using MRM. Popot, et al., Anal Bioanal Chem, 2008, 390:1843-52 (Popot II). The MRM experiments use selected multicharged IGF-I ions (7+ and 8+) as precursor ions in the fragmentation experiments. Bredehöft, et al. reports using an orbitrap mass spectrometric instrument to qualitatively determine the mass to charge ratios of precursor and product ions of IGF-I and use of the identified ions for subsequent IGF-I quantitation using LC-triple quadrupole MS/MS. Bredehöft, et al., Rapid Commun. Mass Spectrom., 2008, 22:477-485.

Similarly, analysis of IGF-II has been reported using enzymatic digestion followed by mass spectrometric analysis of the digestion products. See, e.g., Smith et al., J. Biol. Chem., 1989, 16:9314-9321; and Bayne et al., Peptide Research, 1990, 6:271-273. Other studies have been reported for analysis of mass spectrometric detection of intact IGF-II. See, e.g., Hampton et al., J. Biol. Chem., 1989, 32:19155-19160; Hayne, et al., J. Chromatog. 1991, 52:391-402; Wadensten, et al., Biotech. and App. Biochem., 1991, 13:412-421; Jespersen, et al., J. Mass Spectrom., 1996, 31:893-900; and Nelson, et al., J. Proteome, 2004, 3:851-855. These references report detection of intact IGF-II with plasma desorption and MALDI-TOF mass spectrometric techniques. Hampton et al. detects charge states ranging from 1+ to 3+. All but Hampton et al. detect IGF-II at a 1+ charge state.

SUMMARY OF THE INVENTION

The methods described herein are for mass spectrometric determination of the amount of an insulin-like growth factor I (IGF-I) protein and/or an insulin-like growth factor II (IGF-II) protein in a sample with high resolution/high accuracy mass spectrometry. The methods have simplified pre-analytic steps which only optionally include protein fragmentation, digestion, and/or detection of protein fragments. Preferably, no fragmentation or digestion of the intact protein or proteins is conducted following sample collection.

In a first aspect of the present invention, the amount of an IGF-I protein or fragment thereof in a sample is determined by mass spectrometry methods which include subjecting an IGF-I protein or fragment thereof from the sample to ionization under conditions suitable to produce one or more IGF-I ions detectable by mass spectrometry; and determining the amount of one or more IGF-I ions by high resolution/high accuracy mass spectrometry. The amount of the determined IGF-I ion or ions is related to the amount of the IGF-I protein or fragment thereof in the sample. In some embodiments, the IGF-I protein or fragment thereof is native to the sample. In some embodiments, the IGF-I protein or fragment thereof is intact long R3 IGF-I or a fragment thereof. In some embodiments, the IGF-I protein is intact long R3 IGF-I.

In a second aspect, the amount of an IGF-II protein or fragment thereof in a sample is determined by mass spectrometry methods which include subjecting the IGF-II protein or fragment thereof in the sample to ionization under conditions suitable to produce one or more IGF-II ions detectable by mass spectrometry; and determining the amount of one or more IGF-II ions by high resolution/high accuracy mass spectrometry. The amount of the determined IGF-II ion or ions is related to the amount of the IGF-II protein or fragment thereof in the sample. Preferably, the IGF-II protein is native to the sample and intact.

In a third aspect, the amounts of both an IGF-I protein or fragment thereof and an IGF-II protein or fragment thereof are simultaneously determined by mass spectrometry methods which include subjecting an IGF-I protein or fragment thereof and an IGF-II protein or fragment thereof from the sample to ionization under conditions suitable to produce one or more IGF-I ions and one or more IGF-II ions detectable by mass spectrometry; and determining the amount of one or more IGF-I ions and one or more IGF-II ions by high resolution/high accuracy mass spectrometry. The amount of the determined IGF-I and IGF-II ions are related to the amount of the IGF-I and IGF-II proteins or fragments thereof in the sample. Preferably, the IGF-I and IGF-II proteins are native to the sample and intact.

In some embodiments, the sample may be purified by solid phase extraction (SPE) prior to ionization. In some embodiments, the sample may be purified by high performance liquid chromatography (HPLC) prior to ionization. In related embodiments, the sample may be purified with both SPE and HPLC prior to ionization, and the purification may optionally be conducted with on-line processing.

In some embodiments, the high resolution/high accuracy mass spectrometry is conducted with a resolving power (FWHM) of greater than or equal to about 10,000, such as greater than or equal to about 15,000, such as greater than or equal to about 20,000, such as greater than or equal to about 25,000. In some embodiments, the high resolution/high accuracy mass spectrometry is conducted at an accuracy of less than or equal to about 50 ppm, such as less than or equal to about 20 ppm, such as less than or equal to about 10 ppm, such as less than or equal to about 5 ppm; such as less than or equal to about 3 ppm. In some embodiments, high resolution/high accuracy mass spectrometry is conducted at a resolving power (FWHM) of greater than or equal to about 10,000 and an accuracy of less than or equal to about 50 ppm. In some embodiments, the resolving power is greater than about 15,000 and the accuracy is less than or equal to about 20 ppm. In some embodiments, the resolving power is greater than or equal to about 20,000 and the accuracy is less than or equal to about 10 ppm; preferably resolving power is greater than or equal to about 25,000 and accuracy is less than or equal to about 5 ppm, such as less than or equal to about 3 ppm.

In some embodiments, the high resolution/high accuracy mass spectrometry may be conducted with an orbitrap mass spectrometer, a time of flight (TOF) mass spectrometer, or a Fourier transform ion cyclotron resonance mass spectrometer (sometimes known as a Fourier transform mass spectrometer). In some embodiments, the sample may include a biological sample; preferably plasma or serum.

In some embodiments, the one or more IGF-I ions detectable by mass spectrometry are one or more ions selected from the group consisting of ions with m/z within the ranges of about 850.8±2, 957.1±2, 1093.7±2, and 1275.8±2. Ions within these ranges correspond to IGF-I ions with charges of 9+, 8+, 7+, and 6+, respectively, and predominantly fall within the ranges of the cited m/z values ±1. Preferably the one or more IGF-I ions comprise one or more ions selected from the group consisting of IGF-I ions with m/z within the ranges of 957.1±2 and 1093.7±2. IGF-I ions within the range of 1093.7±2 preferably comprise one or more IGF-I ions selected from the group consisting of IGF-I ions with m/z of about 1091.94±0.1, 1092.80±0.1, 1092.94±0.1, 1093.09±0.1, 1093.23±0.1, 1093.37±0.1, 1093.52±0.1, 1093.66±0.1, 1093.80±0.1, 1093.95±0.1, 1094.09±0.1, 1094.23±0.1, 1094.38±0.1, 1094.52±0.1, 1094.66±0.1, and 1095.37±0.1. In some embodiments, relating the amount of one or more IGF-I ions detected by mass spectrometry to the amount of an IGF-I protein in the sample includes comparison to an internal standard; such as a human or non-human IGF-I protein (e.g., intact recombinant mouse recombinant mouse IGF-I). The internal standard may optionally be isotopically labeled.

In some embodiments, the one or more IGF-II ions detectable by mass spectrometry are one or more IGF-II ions selected from the group consisting of IGF-II ions with m/z within the ranges of about 934.69±2, 1068.07±2, 1245.92±2, and 1494.89±2. Ions within these ranges correspond to IGF-II ions with charges of 8+, 7+, 6+, and 5+, respectively, and predominantly fall within the ranges of the cited m/z values ±1. Preferably the one or more IGF-II ions comprise an IGF-II ion selected from the group consisting of IGF-II ions with m/z of about 1067.36±0.1, 1067.51±0.1, 1067.65±0.1, 1067.80±0.1, 1067.94±0.1, 1068.08±0.1, 1068.23±0.1, 1068.37±0.1, 1068.51±0.1, 1068.65±0.1, 1068.80±0.1, 1068.94±0.1, and 1069.08±0.1; preferably, the one or more IGF-II ions are selected from the group consisting of ions with m/z of about 1067.94±0.1 and 1068.08±0.1. In some embodiments, relating the amount of one or more IGF-II ions detected by mass spectrometry to the amount of IGF-II protein in the sample includes comparison to an internal standard; such as a human or non-human IGF-II protein (e.g., intact recombinant mouse IGF-II).

In some embodiments, the amounts of native intact IGF-I and/or IGF-II in a sample are determined by mass spectrometry methods which include subjecting intact IGF-I and/or IGF-II, native to the sample and purified by solid phase extraction (SPE) and high performance liquid chromatography (HPLC), to ionization under conditions suitable to produce one or more IGF-I and/or IGF-II ions detectable by mass spectrometry. If the amount of native intact IGF-I is determined, the one or more IGF-I ions include one or more IGF-I ions selected from the group consisting of IGF-I ions with m/z within the ranges of about 850.8±2, 957.1±2, 1093.7±2, and 1275.8±2. If the amount of native intact IGF-II is determined, the one or more IGF-II ions include one or more IGF-II ions selected from the group consisting of IGF-II ions with m/z within the ranges of about 934.69±2, 1068.07±2, 1245.92±2, and 1494.89±2. Again, for both IGF-I and IGF-II, ions within the above ranges fall predominantly within the ranges of the indicted m/z value ±1. The amount of the one or more IGF-I and/or IGF-II ions are then determined by high resolution/high accuracy mass spectrometry; wherein the amount of the one or more IGF-I and/or IGF-II ions is used to determine the amount of native intact IGF-I and/or IGF-II in the sample. In these embodiments, the high resolution/high accuracy mass spectrometry is conducted with an orbitrap or TOF mass spectrometer, and SPE and HPLC may be conducted in an on-line fashion.

The features of the embodiments listed above may be combined without limitation for use in methods of the present invention.

In certain preferred embodiments, mass spectrometry is performed in positive ion mode. Alternatively, mass spectrometry is performed in negative ion mode. The preferred ionization technique used in methods described herein is electrospray ionization (ESI). Electrospray ionization may be conducted, for example, with a heated ionization source.

In preferred embodiments, one or more separately detectable internal standards is provided in the sample, the amount of which is also determined in the sample. In these embodiments, all or a portion of both the analyte of interest and the one or more internal standards is ionized to produce a plurality of ions detectable in a mass spectrometer, and one or more ions produced from each are detected by mass spectrometry. The internal standards may be selected from the group consisting of intact non-human IGF-I (e.g., isotopically labeled or unlabeled intact recombinant mouse IGF-I), an isotopically labeled intact human IGF-I protein, an intact non-human IGF-II protein (e.g., isotopically labeled or unlabeled intact recombinant mouse IGF-II), and an isotopically labeled intact human IGF-II protein.

In other embodiments, the amount of an intact IGF-I and/or IGF-II protein in a sample may be determined by comparison to one or more external reference standards. Exemplary external reference standards include blank plasma or serum spiked with an isotopically labeled or unlabeled, intact human or non-human IGF-I and/or IGF-II protein (e.g., isotopically labeled or unlabeled intact recombinant mouse IGF-I and or IGF-II).

In some embodiments, an isotopic signature comprising mass spectrometric peaks from two or more molecular isotopic forms of an analyte may be used to confirm the identity of an analyte being studied. In other embodiments, a mass spectrometric peak from one or more isotopic forms may be used to quantitate the analyte of interest. In some related embodiments, a single the mass spectrometric peak from one isotopic form may be used to quantitate an analyte of interest. In other related embodiments, a plurality of isotopic peaks may be used to quantitate an analyte. The plurality of peaks may be subject to any appropriate mathematical treatment. Several mathematical treatments are known in the art and include, but are not limited to, summing the area under multiple peaks, or averaging the response from multiple peaks.

As used herein, unless otherwise stated, the singular forms "a," "an," and "the" include plural reference. Thus, for example, a reference to "a protein" includes a plurality of protein molecules.

As used herein, the term "IGF-I protein" refers to full-length IGF-I polypeptides or fragments thereof, as well as full-length IGF-I variant polypeptides or fragments thereof. IGF-I variants include, for example, long R3 IGF-I, which is an 83 amino acid analog of IGF-I comprising the complete human IGF-I sequence with the substitution of an Arg(R) for the Glu(E) at position three (hence R3) and a 13 amino acid extension peptide at the N terminus. This analog of IGF-I has been produced with the purpose of increasing the biological activity of the IGF-I peptide. The mass of this analog is about 9111.4 Daltons, thus multiply charged long R3 IGF-I ions may be observed with m/z ratios of about 1014.1±1, 1140.7±1, 1303.5±1, and 1520.6±1. Other IGF-I variant polypeptides are readily recognized by one of skill in the art, including for example full-length IGF-I polypeptides or fragments thereof that have been chemically modified. Exemplary chemical modifications may include reduction of one or more disulfide bridges or alkylation of one or more cystines. These exemplary chemical modifications result in an increase in the mass of an IGF-I variant polypeptide relative to the mass of the corresponding unmodified IGF-I polypeptide. Reduction of one or more disulfide bridges results in a relatively minor change in the mass of the molecule, with the resulting mass to charge ratios falling within the mass to charge ratio ranges described herein. Other chemical modifications that result in a mass deviation from an unmodified IGF-I polypeptide are also encompassed within the meaning of IGF-I protein. One skilled in the art understands that the addition of atoms to an IGF-I protein by chemical modification will result in an observed increase in the mass to charge ratios during mass spectrometry. Thus, IGF-I protein variants that result from chemical modification are included within the meaning IGF-I protein and detectable in accordance with the methods of the invention.

As used herein, the term "IGF-II protein" refers to full-length IGF-II polypeptides or fragments thereof, as well as full-length IGF-II variant polypeptides or fragments thereof. IGF-II variant polypeptides are readily recognized by one of skill in the art, including for example full-length IGF-II polypeptides or fragments thereof that have been chemically modified. Exemplary chemical modifications may include reduction of one or more disulfide bridges or alkylation of one or more cystines. These exemplary chemical modifications result in an increase in the mass of an IGF-II variant polypeptide relative to the mass of the corresponding unmodified IGF-II polypeptide. Reduction of one or more disulfide bridges results in a relatively minor change in the mass of the molecule, with the resulting m/z falling within the m/z ranges described herein. Other chemical modifications that result in a mass deviation from an unmodified IGF-II polypeptide are also encompassed within the meaning of IGF-II protein. One skilled in the art understands that the addition of atoms to an IGF-II protein by chemical modification will result in an observed increase in the mass to charge ratios during mass spectrometry. Thus, IGF-II protein variants that result from chemical modification are included within the meaning IGF-II protein and detectable in accordance with the methods of the invention.

As used here, the term "intact" as describing a polypeptide refers to the full-length (i.e., unfragmented) polypeptide. Intact IGF-I, for example, is a polypeptide containing 70 amino acid residues, and intact long R3 IGF-I is an 83 amino acid analog of IGF-I comprising the complete human IGF-I sequence with the substitution of an Arg(R) for the GLu(E) at position three (hence R3) and a 13 amino acid extension peptide at the N terminus. Non-intact forms of IGF-I and/or IGF-II proteins (i.e., fragments) may also be detected by the methods described herein. For example, fragments of IGF-I and/or IGF-II proteins with a molecular weight of about 1,000 Daltons or larger, such as about 1500 Daltons or larger, such as about 2000 Daltons or larger, such as about 2500 Daltons or larger, such as about 3000 Daltons or larger, such as about 4000 Daltons or larger, such as about 5000 Daltons or larger, such as about 6000 Daltons or larger, such as about 7000 Daltons or larger may be detected by methods described herein.

The term "purification" or "purifying" refers to a procedure that enriches the amount of one or more analytes of interest relative to other components in the sample that may interfere with detection of the analyte of interest. Although not required, "purification" may completely remove all interfering components, or even all material other than the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

The term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample; preferably plasma or serum.

The term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE may operate via a unitary or mixed mode mechanism. As used herein, SPE can be conducted with an extraction column or cartridge such as, for example, a turbulent flow liquid chromatography (TFLC) column. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

The term "chromatography" refers to a process in which a chemical mixture carried by a liquid or gas is separated into components as a result of differential distribution of the chemical entities as they flow through a stationary solid phase.

The term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of separation techniques which employ "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography). In some embodiments, an SPE column may be used in combination with an LC column. For example, a sample may be purified with a TFLC extraction column, followed by additional purification with a HPLC analytical column.

The term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

The term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow, the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

The term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

The terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

The term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring the mass to charge ratio of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

As used herein, the term "resolving power" or "resolving power (FWHM)" (also known in the art as "m/$\Delta m_{50}$%") refers to an observed mass to charge ratio divided by the width of the mass peak at 50% maximum height (Full Width Half Maximum, "FWHM"). The effect of differences in resolving power is illustrated in FIGS. 1A-C, which show theoretical mass spectra of an ion with a m/z of about 1093. FIG. 1A shows a theoretical mass spectrum from a mass analyzer with resolving power of about 3000 (a typical operating condition for a conventional quadrupole mass analyzer). As seen in FIG. 1A, no individual isotopic peaks are discernable. By comparison, FIG. 1B shows a theoretical mass spectrum from a mass analyzer with resolving power of about 10,000, with clearly discernable individual isotopic peaks. FIG. 1C shows a theoretical mass spectrum from a mass analyzer with resolving power of about 12,000. At this highest resolving power, the individual isotopic peaks contain less than 1% contribution from baseline.

As used herein a "unique chemical ion" with respect to mass spectrometry refers a single ion with a single atomic makeup. The single ion may be singly or multiply charged.

As used herein, the term "accuracy" (or "mass accuracy") with respect to mass spectrometry refers to potential deviation of the instrument response from the true m/z of the ion investigated. Accuracy is typically expressed in parts per million (ppm). The effect of differences in mass accuracy is illustrated in FIGS. 2A-D, which show the boundaries of potential differences between a detected m/z and the actual m/z for a theoretical peak at m/z of 1093.52094. FIG. 2A shows the potential range of detected m/z at an accuracy of 120 ppm. By contrast, FIG. 2B shows the potential range of detected m/z at an accuracy of 50 ppm. FIGS. 2C and 2D show the even narrower potential ranges of detected m/z at accuracies of 20 ppm and 10 ppm.

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety. Use of orbitrap analyzers has been reported for qualitative and quantitative analyses of various analytes. See, e.g., U.S. Patent Application Pub. No. 2008/0118932 (filed Nov. 9, 2007); Bredehöft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

The term "operating in negative ion mode" refers to those mass spectrometry methods where negative ions are generated and detected. The term "operating in positive ion mode" as used herein, refers to those mass spectrometry methods where positive ions are generated and detected.

The term "ionization" or "ionizing" refers to the process of generating an ion having a net electrical charge equal to one or more electron units. Negative ions are those having a net negative charge of one or more electron units, while positive ions are those having a net positive charge of one or more electron units.

The term "selective ion monitoring" is a detection mode for a mass spectrometric instrument in which only ions within a relatively narrow mass range, typically about one mass unit or less, are detected.

"Multiple reaction mode," sometimes known as "selected reaction monitoring," is a detection mode for a mass spectrometric instrument in which a precursor ion and one or more fragment ions are selectively detected.

The terms "lower limit of quantification", "lower limit of quantitation" or "LLOQ" refer to the point where measurements become quantitatively meaningful. The analyte response at this LLOQ is identifiable, discrete and reproducible with a relative standard deviation (RSD %) of less than 20% and an accuracy of 85% to 115%.

The term "limit of detection" or "LOD" is the point at which the measured value is larger than the uncertainty associated with its measurement. The LOD is defined as four times the RSD of the mean at the zero concentration.

The term "simultaneous" as applied to simultaneously detecting the amount of two or more analytes from a sample means acquiring data reflective of the amount of the two or more analytes in the sample from the same sample injection. The data for each analyte may be acquired sequentially or in parallel, depending on the instrumental techniques employed. For example, a single sample containing two analytes, such as intact IGF-I and IGF-II proteins, may be injected into a HPLC column, which may then elute each analyte one after the other, resulting in introduction of the analytes into a mass spectrometer sequentially. Determining the amount of each of these two analytes is simultaneous for the purposes herein, as both analytes result from the same sample injection into the HPLC.

An "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 15A shows the TIC.

DETAILED DESCRIPTION OF THE INVENTION

Figure 1A:
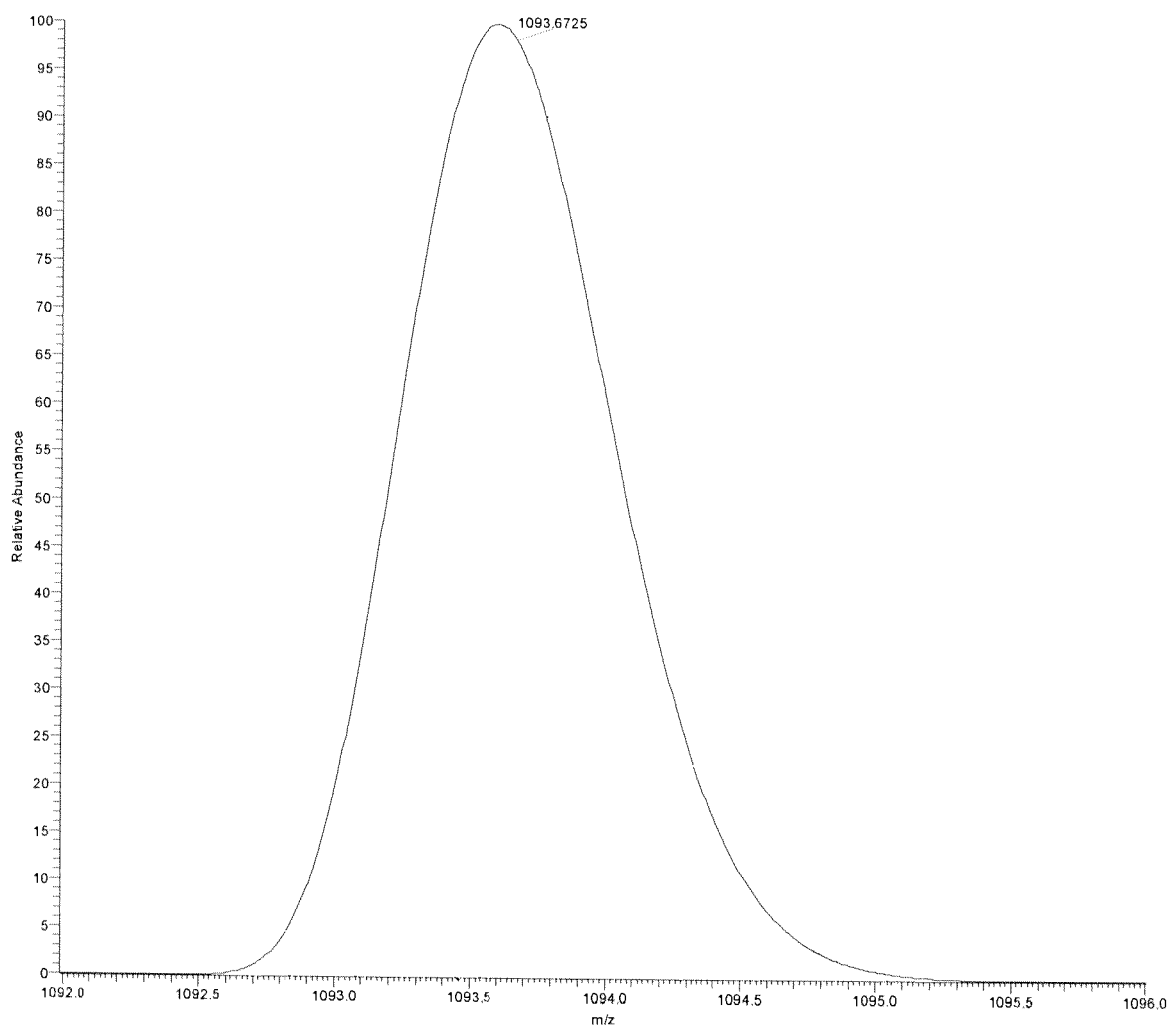
FIGS. 1A-C show theoretical mass spectra of an ion with a m/z of about 1093 as analyzed by a mass analyzer with resolving power of about 3000 (FIG. 1A), about 10,000 (FIG. 1B), and about 12,000 (FIG. 1C).
Figure 1B:
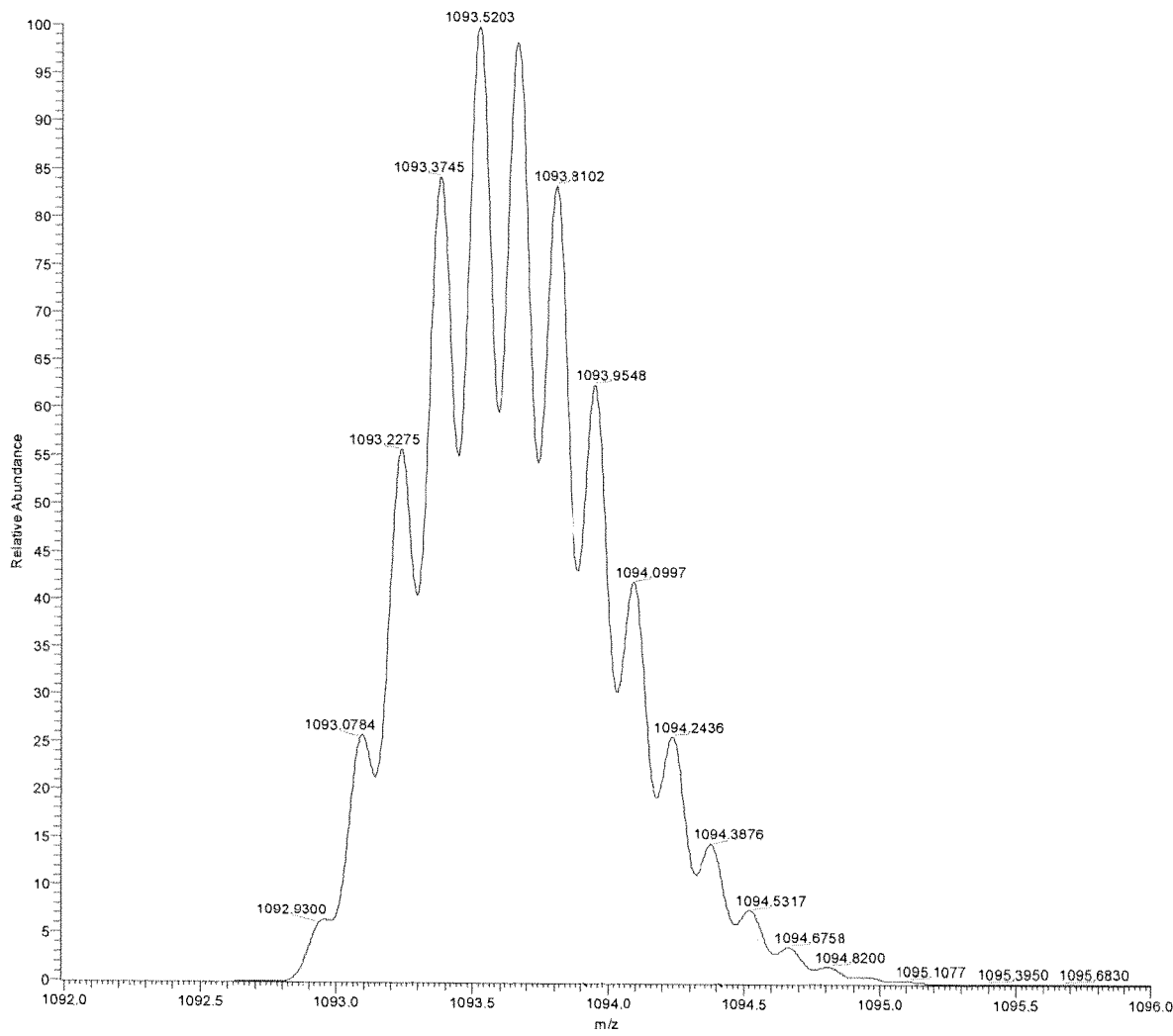
Figure 1C:
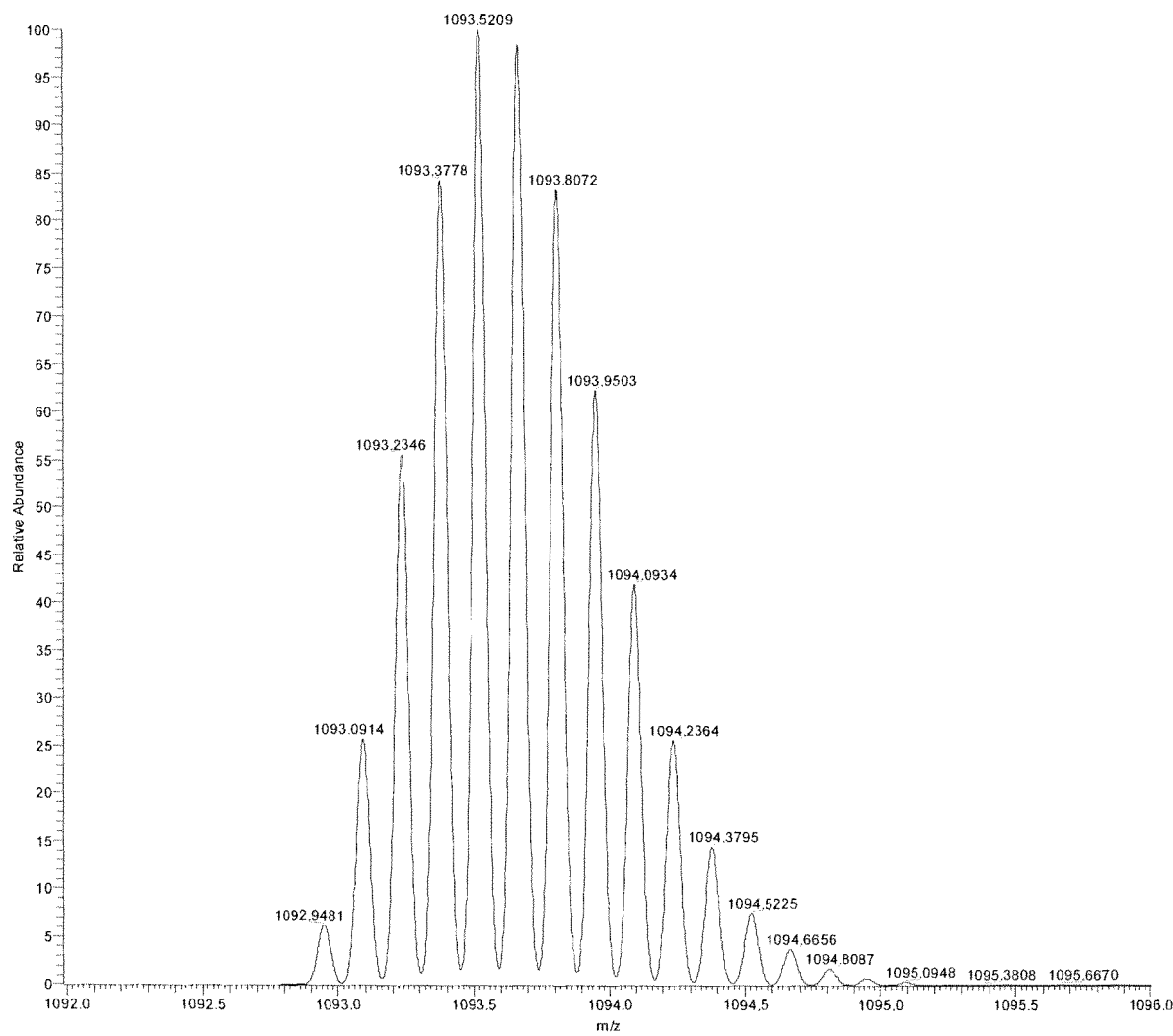
Figure 2A:
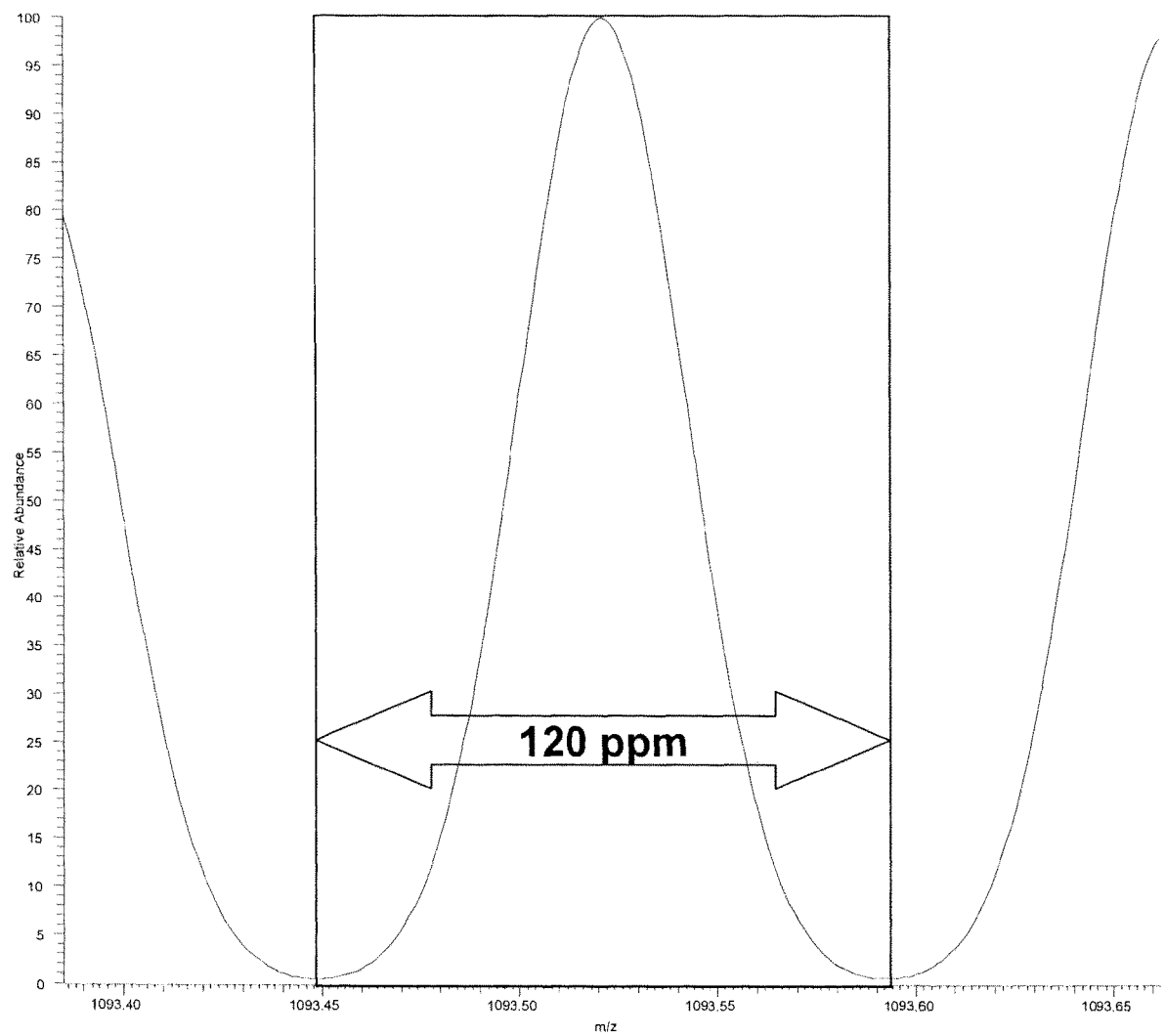
FIGS. 2A-D show potential deviation of instrument response from the true m/z of the ion investigated for a theoretical peak at m/z of 1093.52094 at a mass accuracy of 120 ppm (FIG. 2A), a mass accuracy of 50 ppm (FIG. 2B), a mass accuracy of 20 ppm (FIG. 2C), and at a mass accuracy of 10 ppm (FIG. 2D).
Figure 2B:
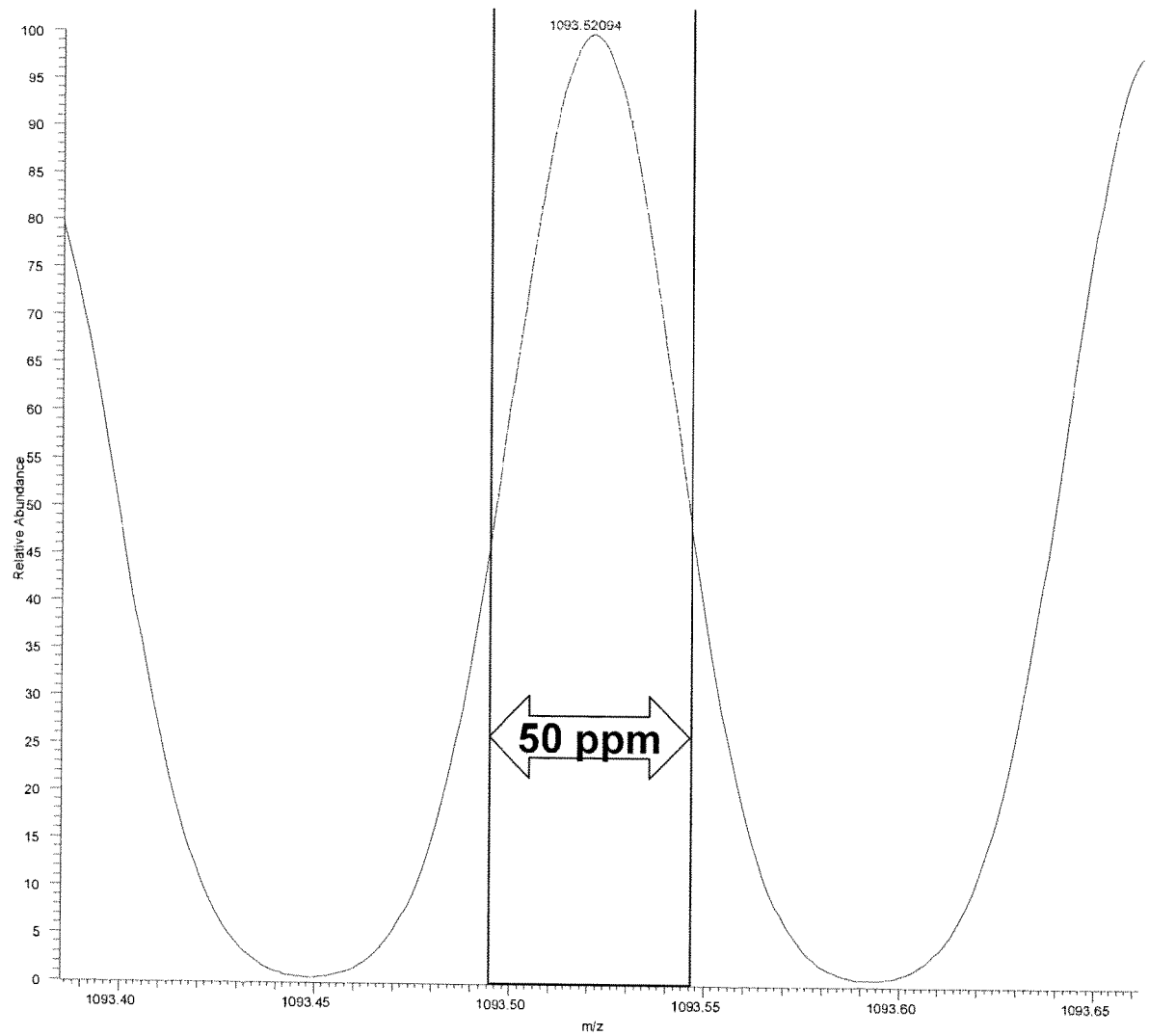
Figure 2C:
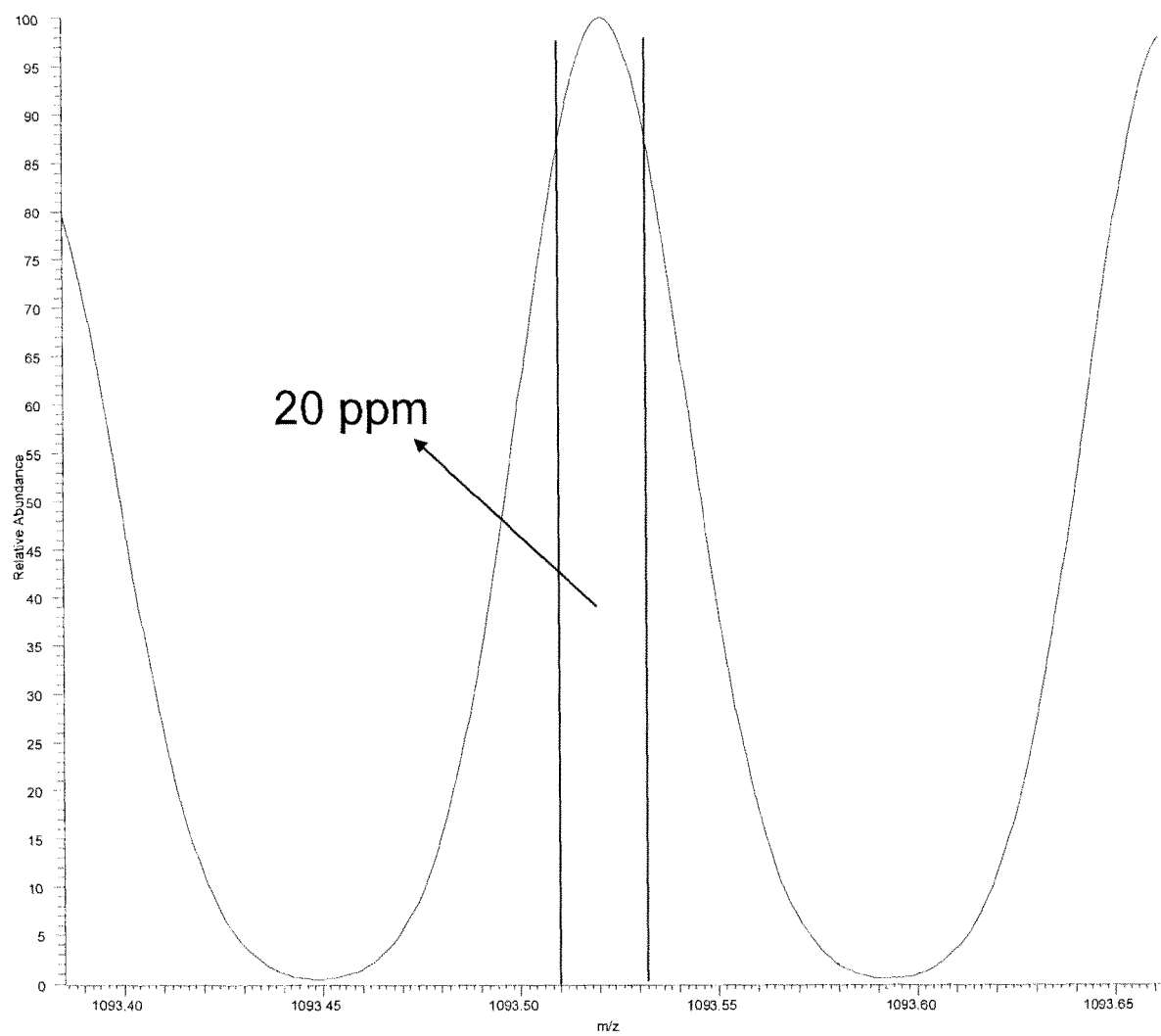
Figure 2D:
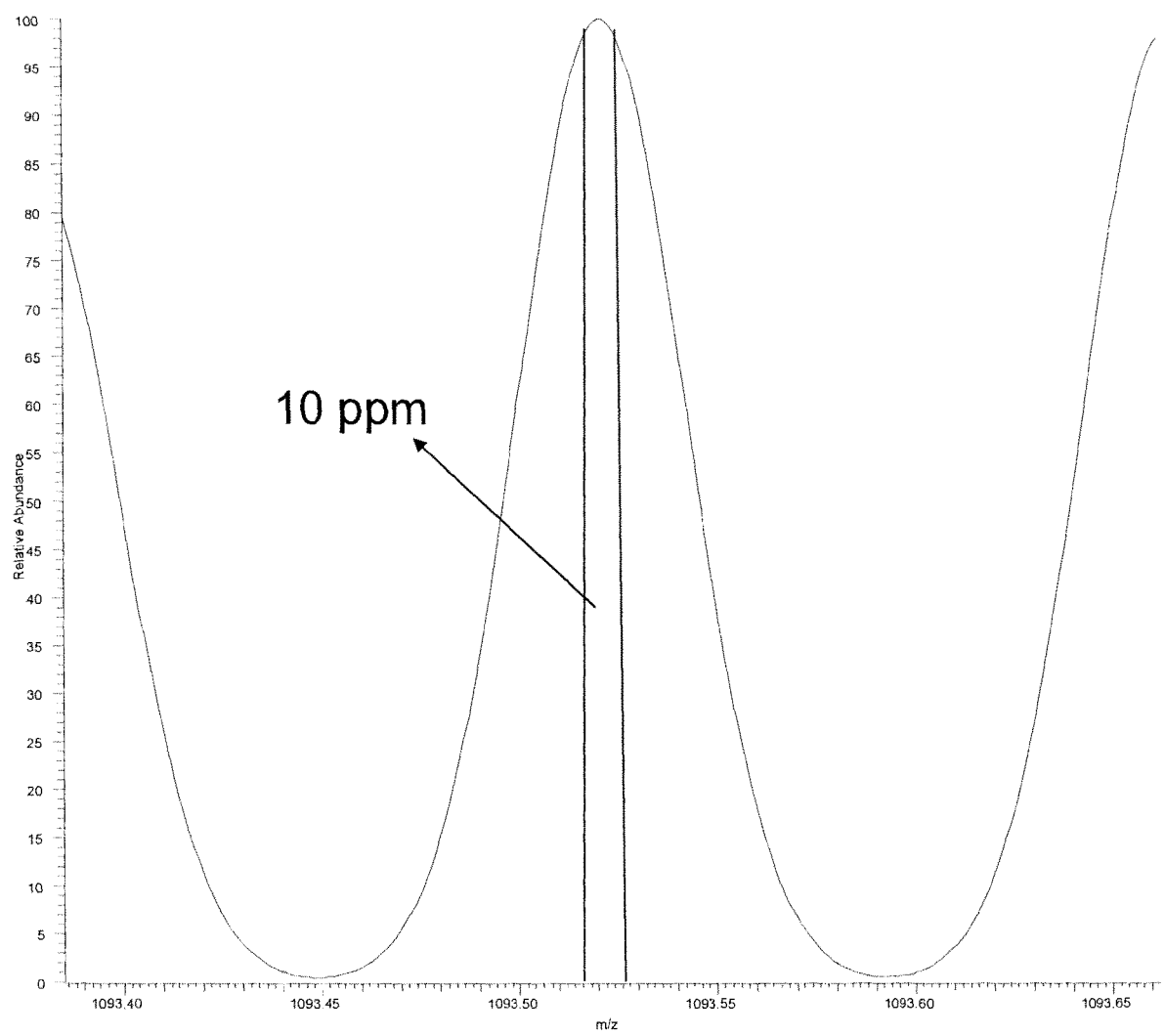

Methods are described for measuring the amount of an IGF-I and/or IGF-II protein. More specifically, high accuracy/high resolution mass spectrometric methods are described for ionizing intact IGF-I and/or intact IGF-II, or fragments thereof, and detecting ions produced thereby. These methods may include purifying intact IGF-I and/or intact IGF-II, or fragments thereof, in the sample prior to ionization and mass spectrometry. However, the methods may be performed without purifying the sample with chromatography. Preferred embodiments are particularly well suited for application in large clinical laboratories for automated intact IGF-I and/or intact IGF-II, or fragment, quantification. Additionally, certain embodiments presented herein provide methods for IGF-I and/or IGF-II quantitation that are insensitive to interference from binding proteins that may also be present in the sample, such as, for example, IGFBP-3.

While the examples discussed below demonstrate quantitation of intact human IGF-I and/or IGF-II, other IGF-I and/or IGF-II proteins may also be analyzed by the methods described herein. For example, intact non-human IGF-I and/or IGF-II (e.g., isotopically labeled or unlabeled intact recombinant mouse IGF-I and/or IGF-II), isotopically labeled intact human IGF-I and/or IGF-II, or long R3 IGF-I, or fragments thereof, in suitable test samples may all be quantitated with the following methods.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition.

The present invention also contemplates kits for an IGF-I and/or IGF-II protein quantitation assay. A kit for an IGF-I and/or IGF-II protein quantitation assay may include a kit comprising the compositions provided herein. For example, a kit may include packaging material and measured amounts of an isotopically labeled internal standard in amounts sufficient for at least one assay. Typically, the kits will also include instructions recorded in a tangible form (e.g., contained on paper or an electronic medium) for using the packaged reagents for use in an IGF-I and/or IGF-II protein quantitation assay.

Quality control (QC) pools having known concentrations, for use in embodiments of the present invention, are preferably prepared using a matrix similar to the intended sample matrix.

Sample Preparation for Mass Spectrometric Analysis

In preparation for mass spectrometric analysis, an IGF-I protein may be enriched relative to one or more other components in the sample (e.g. other proteins) by various methods known in the art, including for example, solid phase extraction (SPE), LC, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like. In some embodiments, liquid chromatography and/or SPE, and/or protein precipitation may be used in combination.

Protein precipitation is one method of preparing a test sample, especially a biological sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving IGF-I and/or IGF-II proteins in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to solid phase extraction and/or liquid chromatography and subsequent mass spectrometry analysis. In certain embodiments, the use of protein precipitation such as for example, acid ethanol protein precipitation, may obviate the need for TFLC, SPE, or other on-line extraction prior to mass spectrometry or HPLC and mass spectrometry.

In preferred embodiments, liquid-liquid extraction methods (such as acid ethanol extraction) are used to extract native intact IGF-I and/or IGF-II from a sample. In these embodiments, between 10 µl and 500 µl of sample, such as between 25 µl and 250 µl, such as about 100 µl, is added to a portion of extraction solvent. The quantity of extraction solvent is commensurate with sample volume and may vary depending on the extraction solvent used, but is preferably between about 50 µl and 1000 µl. The sample/solvent mixtures are mixed and centrifuged, and a portion of the supernatant or organic phase (depending on solvent used) is drawn off for further analysis. Solvent may be removed from the drawn off portion, for example under a nitrogen flow, and the residue reconstituted in a different solvent from that used for the liquid-liquid extraction. At least a portion of the resulting solution may then be subjected to additional processing steps, such as SPE and/or LC, prior to mass spectrometry.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with IGF-I and/or IGF-II. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a C-18 alkyl bonded column (such as a Phenomenex Onyx monolithic C-18 column). The chromatographic column includes an inlet port for receiving a sample and an outlet port for discharging an effluent that includes the fractionated sample. The sample may be supplied to the inlet port directly, or from a SPE column, such as an on-line SPE guard cartridge or a TFLC column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In some embodiments, HPLC is conducted with an alkyl bonded analytical column chromatographic system. In certain embodiments, a C-18 analytical column (e.g., Phenomenex Onyx Monolithic C18, or equivalent) is used. In certain embodiments, HPLC and/or TFLC are performed using HPLC Grade 0.2% formic acid in water as mobile phase A and 0.2% formic acid in acetonitrile as mobile phase B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of an IGF-I protein or fragment prior to mass spectrometry. In such embodiments, samples may be extracted using a TFLC column which captures the analyte, then eluted and chromatographed on a second TFLC column or on an analytical HPLC column prior to ionization. For example, sample extraction with a TFLC extraction column may be accomplished with a large particle size (50 µm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, protein precipitation is accomplished with acid ethanol extraction from serum, and the resulting solution is subjected to SPE, preferably conducted on-line with a C-18 extraction column (e.g., a Phenomenex Onyx C-18 guard cartridge, or equivalent). The eluent from the SPE column may then be applied to an analytical LC column, such as a HPLC column in an on-line fashion, prior to mass spectrometric analysis.

Detection and Quantitation by Mass Spectrometry

Mass spectrometry is performed using a mass spectrometer, which includes an ion source for ionizing a sample and creating charged molecules for further analysis. In various embodiments, an IGF-I and/or IGF-II protein may be ionized by any suitable method known to the skilled artisan. For example, ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. Depending on the particular ionization method and conditions employed, IGF-I and IGF-II proteins may be ionized to a number of different charge states. The ionization source may be selected to minimize the dispersion of charge states generated. In some embodiments, ESI (optionally heated) is used as the ionization source, and the ionization conditions are optimized to minimize the disbursement of observed multiply charged IGF-I and/or IGF-II protein ions.

IGF-I and/or IGF-II proteins may be ionized in positive or negative mode. In preferred embodiments, one or more IGF-I and/or IGF-II proteins are ionized in positive mode. In some embodiments, multiply charged intact IGF-I ions are generated with m/z ratios within the ranges of about 850.8±2, 957.1±2, 1093.7±2, and 1275.8±2. In some embodiments, multiply charged intact IGF-II ions are generated with m/z ratios within the ranges of about 934.69±2, 1068.07±2, 1245.92±2, and 1494.89±2. The majority of the generated multiply charged ions within these ranges may fall within a narrower sub-range, such as the indicated m/z ±1.

In mass spectrometry techniques generally, after the sample has been ionized, the positively or negatively charged ions thereby created may be analyzed to determine a mass to charge ratio (m/z). Various analyzers for determining m/z include quadrupole analyzers, ion trap analyzers, and time-of-flight analyzers, and orbitrap analyzers. According to methods of the present invention, high resolution/high accuracy mass spectrometry is used for quantitative analysis of IGF-I and/or IGF-II proteins. That is, mass spectrometry is conducted with a mass spectrometer capable of exhibiting a resolving power (FWHM) of at least 10,000, with accuracy of about 50 ppm or less for the ions of interest; preferably the mass spectrometer exhibits a resolving power (FWHM) of 20,000 or better and accuracy of about 20 ppm or less; such as a resolving power (FWHM) of 25,000 or better and accuracy of about 5 ppm or less; such as a resolving power (FWHM) of 25,000 or better and accuracy of about 3 ppm or less. Three exemplary mass spectrometers capable of exhibiting the requisite level of performance for IGF-I and/or IGF-II protein ions are those which include orbitrap mass analyzers, certain TOF mass analyzers, or Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring carbon containing molecules will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron≈1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2 (difference of 1 amu/charge state of 5). High resolution/high accuracy mass spectrometers are capable of discerning between isotopic forms of highly multiply charged ions (such as ions with charges of ±5, ±6, ±7, ±8, ±9, or higher).

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z ratios and relative abundances for two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks or averaging the response from multiple peaks.

Figure 4:
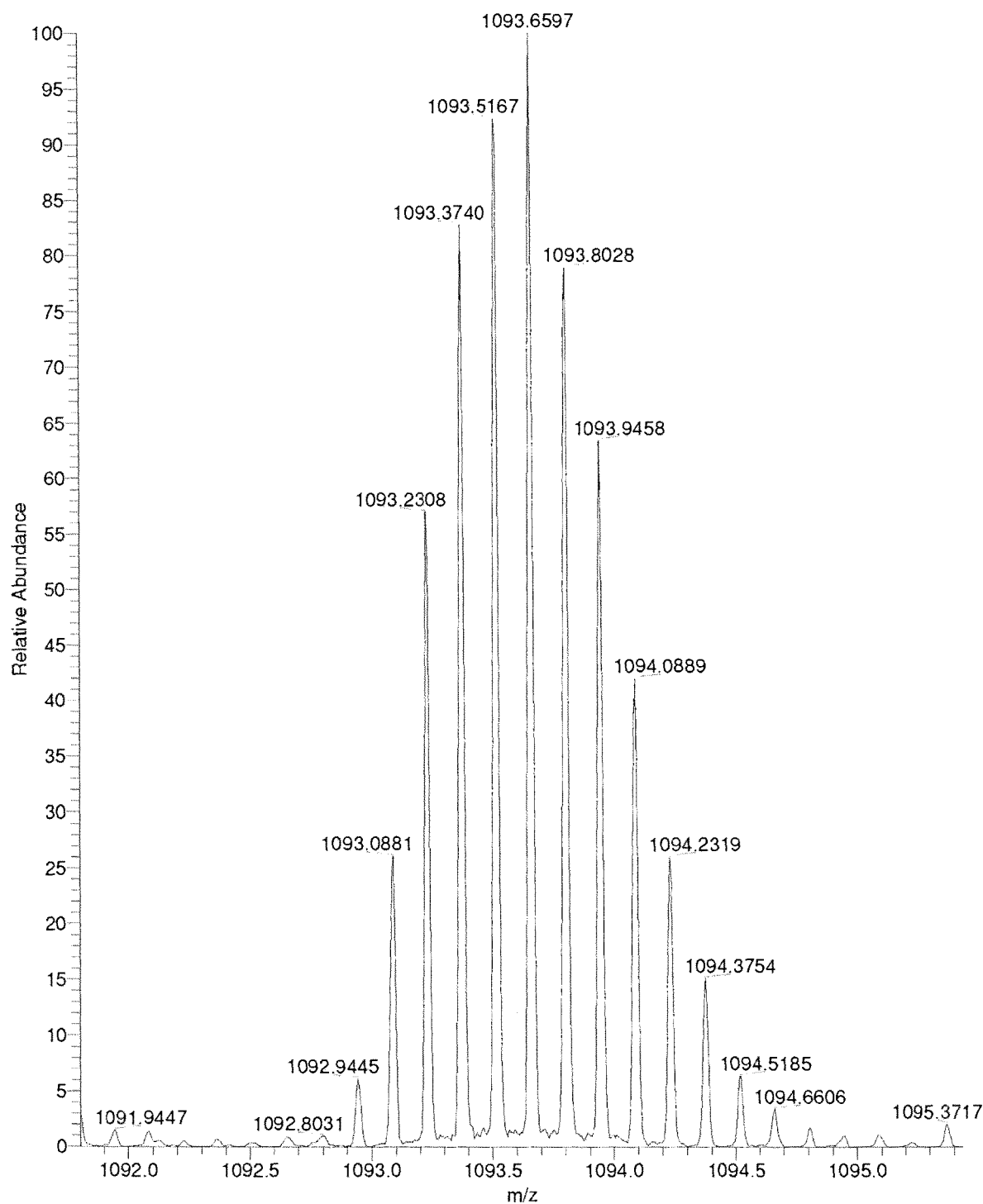
FIG. 4 shows an exemplary spectrum across a m/z range of about 1091 to 1096 for intact IGF-I generated with an orbitrap mass spectrometer. Details are discussed in Example 2.

An exemplary spectrum demonstrating such multiple isotopic forms of IGF-I ions within a m/z range of about 1091-1095.5 is seen in FIG. 4. As seen in the exemplary spectrum, peaks from various isotopic forms are observed at m/z of about 1091.9447, 1092.8031, 1092.9445, 1093.0881, 1093.2308, 1093.3740, 1093.5167, 1093.6597, 1093.8028, 1093.9458, 1094.0889, 1094.2319, 1094.3754, 1094.5185, 1094.6606, and 1095.3717. Note, however, that the precise masses observed for isotopic variants of any ion may vary slightly (e.g., ±0.1) because of instrumental variance.

Figure 12:
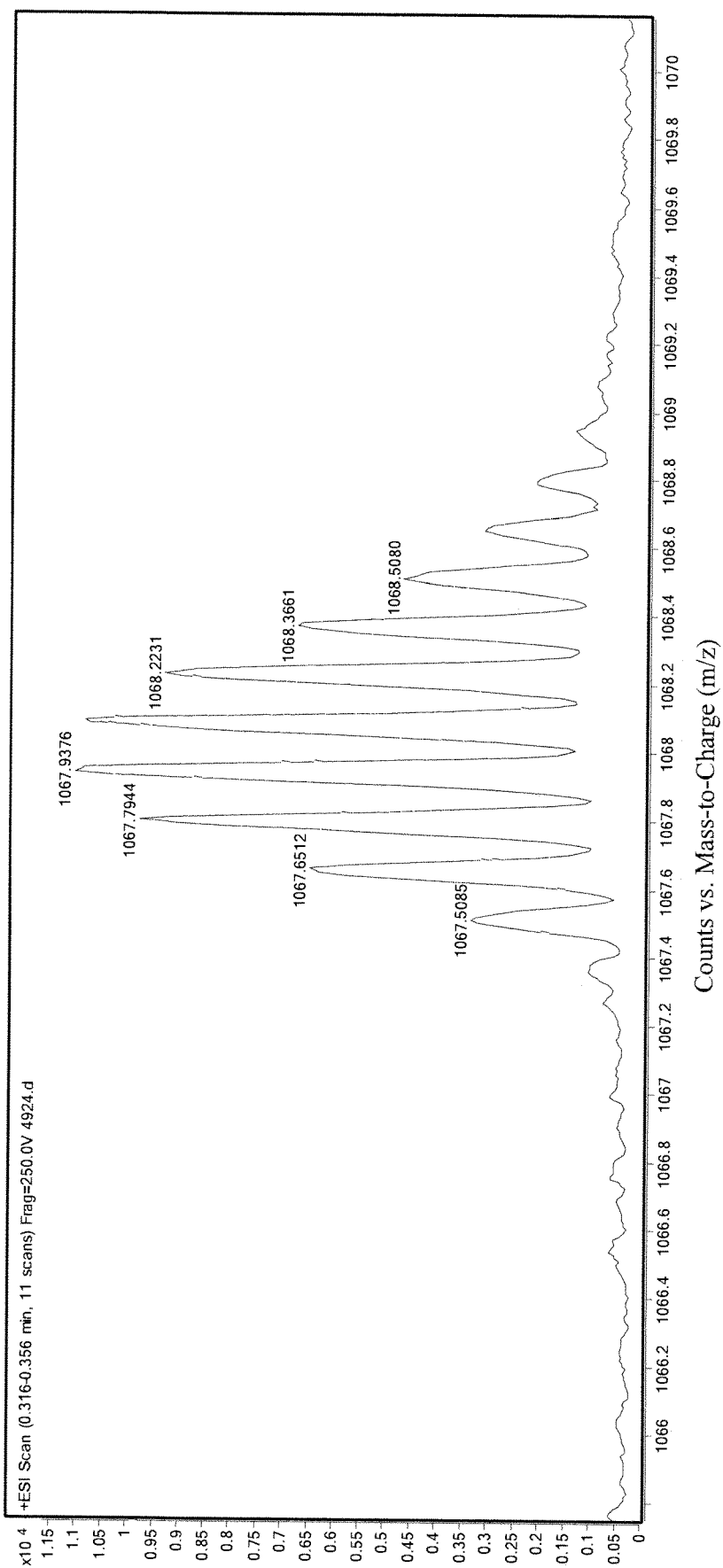
FIG. 12 shows an exemplary spectrum across a m/z range of about 1066 to 1070 for intact IGF-II generated with an high resolution/high accuracy TOF mass spectrometer. Details are discussed in Example 11.

Another exemplary spectrum demonstrating such multiple isotopic forms of IGF-II ions within a m/z range of about 1067.0-1069.5 is seen in FIG. 12. As seen in the exemplary spectrum, peaks from various isotopic forms are observed at m/z of about 1067.36, 1067.51, 1067.65, 1067.80, 1067.94, 1068.08, 1068.23, 1068.37, 1068.51, 1068.65, 1068.80, 1068.94, and 1068.08. Again, the precise masses observed for isotopic variants of any ion may vary slightly because of instrumental variance.

In mass spectrometric techniques generally, ions may be detected using several detection modes. For example, selected ions may be detected, i.e. using a selective ion monitoring mode (SIM), or alternatively, ions may be detected using a scanning mode. When operated in a scanning mode, the mass spectrometer typically provides the user with an ion scan; that is, the relative abundance of each ion with a particular mass/charge over a given range (e.g., 100 to 1000 amu). Further, when using instruments capable of multiple mass spectrometric events, such as certain ion trap or triple quadrupole instruments, mass transitions resulting from collision induced dissociation or neutral loss may be monitored, e.g., multiple reaction monitoring (MRM) or selected reaction monitoring (SRM).

The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, internal or external standards may be run with the samples, and a standard curve constructed based on ions generated from those standards. Using such a standard curve, the relative abundance of a given ion may be converted into an absolute amount of the original molecule. In certain preferred embodiments, one or more standards are used to generate a standard curve for calculating the quantity of an IGF-I and/or IGF-II protein. Methods of generating and using such standard curves are well known in the art and one of ordinary skill is capable of selecting an appropriate internal standard. For example, in preferred embodiments isotopically labeled or unlabeled intact non-human IGF-I and/or IGF-II (e.g., recombinant mouse IGF-I and/or IGF-II) or isotopically labeled intact human IGF-I and/or IGF-II may be used as a standard. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. The isotopic label can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In some embodiments, intact IGF-I and/or IGF-II in a sample are detected and/or quantified using MS as follows. The samples are subjected to liquid chromatography, preferably HPLC; the flow of liquid solvent from a chromatographic column enters a heated nebulizer interface of an ESI ionization source; and the solvent/analyte mixture is converted to vapor in the heated charged tubing of the interface. The analyte (e.g., intact IGF-I and/or IGF-II) contained in the solvent, is ionized by applying a large voltage to the solvent/analyte mixture. As the analyte exits the charged tubing of the interface, the solvent/analyte mixture nebulizes and the solvent evaporates, leaving analyte ions in various charge states. Quantitative data is then collected for the intensity of one or more of ions. The quantitative data for signal intensity for one or more ions is then collected and related to the quantity of intact IGF-I and/or IGF-II in the sample.

Figure 3:
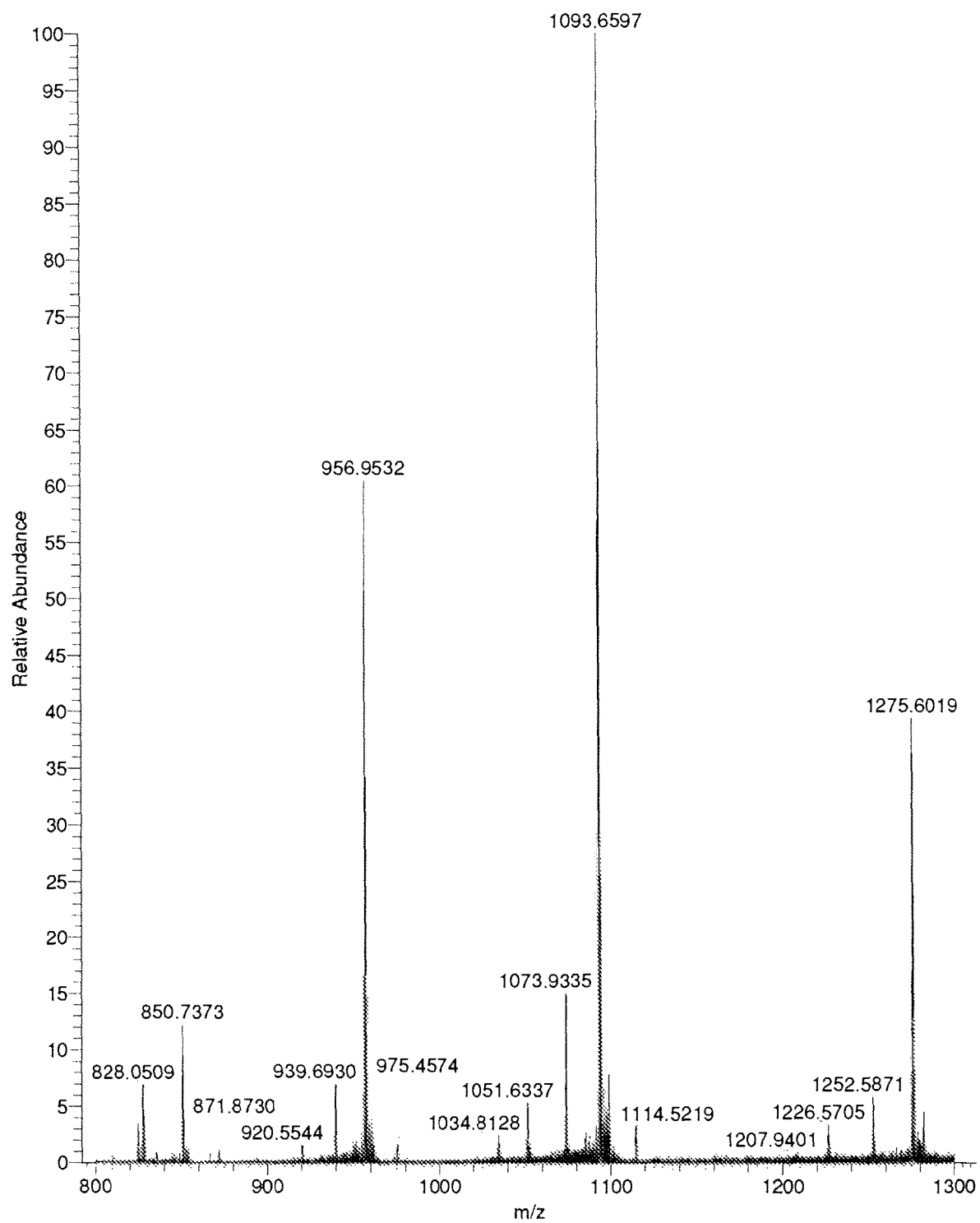
FIG. 3 shows an exemplary spectrum across a m/z range of about 800 to 1300 for intact IGF-I generated with an orbitrap mass spectrometer. Details are discussed in Example 2.

For intact IGF-I, ions in various charge states may be observed with m/z within the ranges of about 850.8±2 (9+), 957.1±2 (8+), 1093.7±2 (7+), and 1275.8±2 (6+). In some embodiments, data from one or more IGF-I ions with m/z within the range of about 1093.7±2 is collected and used for quantitation. Exemplary ions within this m/z range include IGF-I ions with m/z of about 1091.9±0.1, 1092.8±0.1, 1092.9±0.1, 1093.1±0.1, 1093.2±0.1, 1093.4±0.1, 1093.5±0.1, 1093.7±0.1, 1093.8±0.1, 1093.9±0.1, 1094.1±0.1, 1094.2±0.1, 1094.4±0.1, 1094.5±0.1, 1094.7±0.1, and 1095.4±0.1. This listing is not meant to be limiting. Numerous other ions may be suitable for use in the instant methods, as demonstrated in the spectrum shown in FIG. 3 (which demonstrates detection of groups of isotopic ions at m/z of about 828.0509±2, 850.7373±2, 871.8730±2, 920.5544±2, 939.6930±2, 956.9532±2, 975.4576±2, 1034.8128±2, 1051.6337±2, 1073.9335±2, 1093.6597±2, 1114.5219±2, 1207.9401±2, 1226.5705±2, 1252.5871±2, and 1275.6019±2; note, however, that as above, the ions of individual isotopes within these ranges will predominantly fall within the ranges of the indicated m/z ±1. Also, at this level of precision, masses observed for any ion may vary slightly because of instrumental variance, e.g. ±0.1).

For intact IGF-II, ions various charge states may be observed with m/z within the ranges of about 934.69±2 (8+), 1068.07±2 (7+), 1245.92±2 (6+), and 1494.89±2 (5+). In some embodiments, data from one or more IGF-II ions with m/z within the range of about 1068.07±2 is collected and used for quantitation. Exemplary ions within this m/z range include IGF-II ions with m/z of about 1067.36±0.1, 1067.51±0.1, 1067.65±0.1, 1067.80±0.1, 1067.94±0.1, 1068.08±0.1, 1068.23±0.1, 1068.37±0.1, 1068.51±0.1, 1068.65±0.1, 1068.80±0.1, 1068.94±0.1, and 1069.08±0.1. In some embodiments, the one or more IGF-II ions are selected from the group consisting of IGF-II ions with m/z of about 1067.94±0.1 and 1068.08±0.1. This listing is not meant to be limiting and other ions may be suitable for use in the instant methods.

In some embodiments, the use of a high resolution/high accuracy mass spectrometer may allow for the signal intensity of a peak from a single isotopic form of a single ion (such as the single IGF-I ion peak shown in FIG. 4 at m/z of about 1093.66, or the single IGF-II peak shown in FIG. 12 at m/z of about 1067.80) to be selected for data acquisition. Alternatively, quantitative data for signal intensity from one or more isotopic forms of a single ion (such as one or more IGF-I or IGF-II isotopic forms as demonstrated in FIGS. 4 and 12), or signal intensity across a narrow m/z range (such as all IGF-I signal intensity for a m/z range of about 1093.7±1, or all IGF-II signal intensity for a m/z range of about 1068.2±1), may be collected and related to the quantity of intact IGF-I and/or IGF-II in the sample.

In some embodiments, quantitative data for signal intensity is collected for one or more IGF-I and/or IGF-II ions from at least two different charge states. The intensities of these ions may then be used for quantitative assessment of intact IGF-I and/or IGF-II in the sample. For example, IGF-I may be quantitated with signal intensity from one or more IGF-I ions at the 8+ charge state (i.e., IGF-I ions within a m/z range of about 957.1±2) and one or more IGF-I ions at the 7+ charge state (i.e., IGF-I ions within a m/z range 1093.7±2). In embodiments where quantitative data for signal intensity of two or more ions are collected, the intensities may be combined by any mathematical method known in the art (such as summation, or averaging the area under the curves) for quantitative assessment of intact IGF-I and/or IGF-II in the sample.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks are measured to determine the amount of an IGF-I and/or IGF-II protein or fragment. As described above, the relative abundance of a given ion may be converted into an absolute amount of the original analyte using calibration standard curves based on peaks of one or more ions of an internal molecular standard.

In some embodiments, IGF-I and IGF-II are quantitated simultaneously. In these embodiments, each IGF-I and IGF-II may each be quantitated by any of the methods provided above.

In certain preferred embodiments, the lower limit of quantitation (LLOQ) for IGF-I is within the range of about 15.0 ng/mL to 200 ng/dL, inclusive; preferably within the range of about 15.0 ng/dL to 100 ng/mL, inclusive; preferably within the range of about 15.0 ng/mL to 50 ng/mL, inclusive; preferably within the range of about 15.0 ng/mL to 25 ng/mL, inclusive; preferably within the range of about 15.0 ng/mL to 15 ng/mL, inclusive; preferably within the range of about 15.0 ng/mL to 10 ng/mL, inclusive; preferably about 15.0 ng/mL.

In certain preferred embodiments, the lower limits of quantitation (LLOQ) for IGF-II is within the range of about 30.0 ng/mL to 200 ng/dL, inclusive; preferably within the range of about 30.0 ng/dL to 100 ng/mL, inclusive; preferably within the range of about 30.0 ng/mL to 50 ng/mL, inclusive; preferably within the range of about 30.0 ng/mL to 25 ng/mL, inclusive; preferably within the range of about 30.0 ng/mL to 15 ng/mL, inclusive; preferably within the range of about 30.0 ng/mL to 10 ng/mL, inclusive; preferably about 30.0 ng/mL.

In certain preferred embodiments, the limit of detection (LOD) for IGF-I is within the range of about 4.9 ng/mL to 200 ng/mL, inclusive; preferably within the range of about 4.9 ng/mL to 100 ng/mL, inclusive; preferably within the range of about 4.9 ng/mL to 50 ng/mL, inclusive; preferably within the range of about 4.9 ng/mL to 25 ng/mL, inclusive; preferably within the range of about 4.9 ng/mL to 20 ng/mL, inclusive; preferably about 4.9 ng/mL.

In certain preferred embodiments, the limits of detection (LOD) for IGF-II is within the range of about 8.2 ng/mL to 200 ng/mL, inclusive; preferably within the range of about 8.2 ng/mL to 100 ng/mL, inclusive; preferably within the range of about 8.2 ng/mL to 50 ng/mL, inclusive; preferably within the range of about 8.2 ng/mL to 25 ng/mL, inclusive; preferably within the range of about 8.2 ng/mL to 20 ng/mL, inclusive; preferably about 8.2 ng/mL.

The following Examples serve to illustrate the invention. These Examples are in no way intended to limit the scope of the methods. In particular, the following Examples demonstrate quantitation of IGF-I and IGF-II proteins or fragments by mass spectrometry with the use of a particular an internal standard. The use of the indicated internal standard is not meant to be limiting in any way. Any appropriate chemical species, easily determined by one in the art, may be used as an internal standard.

EXAMPLES

Example 1: Enrichment of IGF-I Proteins or Fragments

Intact IGF-I was extracted from serum samples using a combination of sample preparation and subsequent on-line SPE. Acid ethanol extraction was conducted as follows.

100 µL of each serum sample was treated with 400 µL of acid/ethanol (87.5% EtOH/12.5% 2M HCl) to form a precipitate. The mixture was subject to centrifugation to obtain a supernatant and pellet. 400 µL of supernatant is then withdrawn and mixed with 60 µL 1.5M Tris base. Any precipitate that formed with the addition of the Tris base was filtered out and discarded. The filtrate was diluted with an on-line dilution system with 5% formic acid in water to reduce the ethanol concentration to sufficient levels that the IGF-I in solution would bind to an extraction column.

The diluted extracted samples were injected into a Cohesive LC system for on-line SPE and HPLC processing prior to mass spectrometric analysis. On-line extraction and enrichment of IGF-I was accomplished using a Phenomenex Monolithic Onyx C18 Guard Cartridge (10×4.6 mm) as an on-line SPE column. Analytical separation was accomplished by HPLC with a Phenomenex Onyx Monolithic C18 column (50×2.0 mm).

Example 2: Detection and Quantitation of Intact IGF-I with High Resolution/High Accuracy Orbitrap MS MS was performed using a Thermo Exactive MS system (Thermo Electron Corporation). This system employs an orbitrap MS analyzer capable of high resolution/high accuracy MS. The instrument exhibited resolving power of approximately 25,000 FWHM, and mass accuracy of approximately 1 ppm while measuring intact IGF-I.

Ionization was conducted with an ESI source in positive ion mode. Species of multiply charged intact IGF-I ions were observed with m/z of about 851, 957, 1094, and 1275, corresponding to the $[IGF-I+nH]^{n+}$ (n=9+, 8+, 7+, and 6+, respectively) ions. Full scan spectra and an enlarged portion of this spectra showing the isotopic signature of the 1094 ion are found in FIGS. 3 and 4, respectively.

Figure 5:
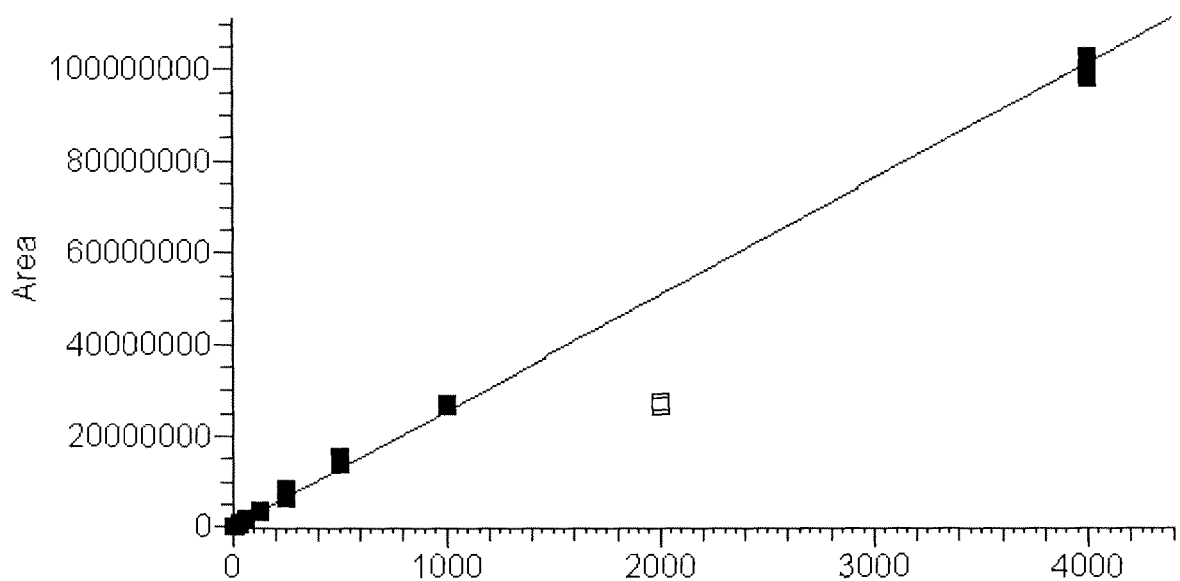
FIG. 5 shows a plot of analytical results for various on-column quantities of intact IGF-I. Details are discussed in Example 2.

Data collected for single isotopic forms of the two strongest ions, corresponding to isotopic forms of ions with m/z of about 956.9532 and 1093.6592, were summed and use to quantitatively assess the amount of intact IGF-I in the samples. Linearity was observed in a calibration curve prepared from 31 fmol to 4000 fmol on column of intact IGF-I. This curve is shown in FIG. 5. The goodness of fit ($R^2$) value for the native intact IGF-I was 0.9984.

Example 3: Detection and Quantitation of Intact IGF-I with High Resolution/High Accuracy TOF MS MS was also performed using an Agilent 6530 Accurate-Mass Q-TOF MS system (Agilent Technologies, Inc.). This system employs a high resolution/high accuracy TOF MS analyzer capable of high resolution/high accuracy MS. The instrument exhibited resolving power of approximately 25,000 FWHM, and mass accuracy of approximately 3 ppm while measuring intact IGF-I. The following software was used for these experiments: Agilent MassHunter Workstation Acquisition B.02.01; Agilent MassHunter Quantitative Software B.03.02; Agilent MassHunter Qualitative software B.02.00; and Cohesive Aria OS v.1.5.1.

Figure 6A:
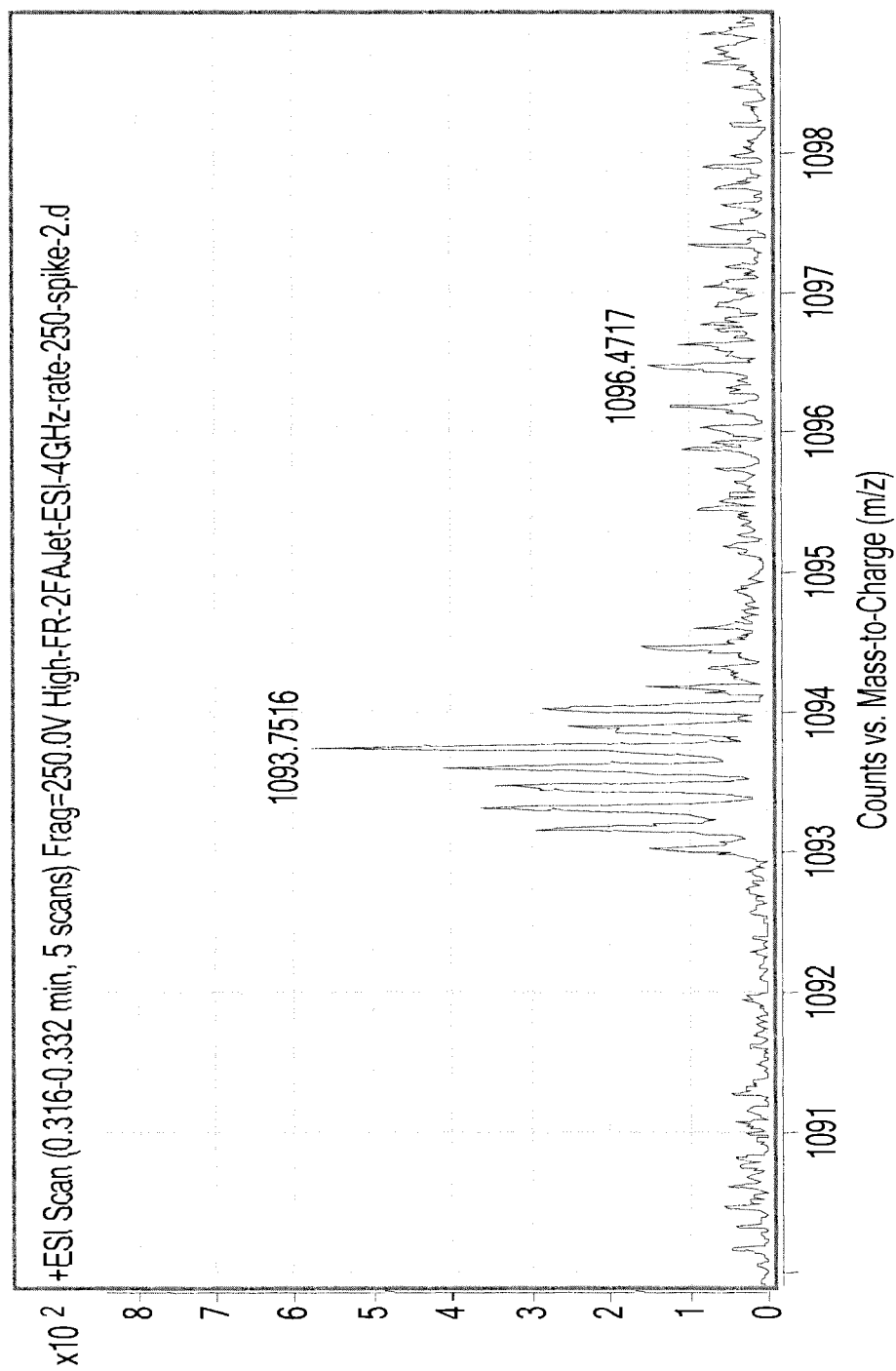
FIG. 6A shows an exemplary spectrum for about 40 fmol (on-column) intact IGF-I across a m/z range of about 1090 to 1098.
Figure 6B:
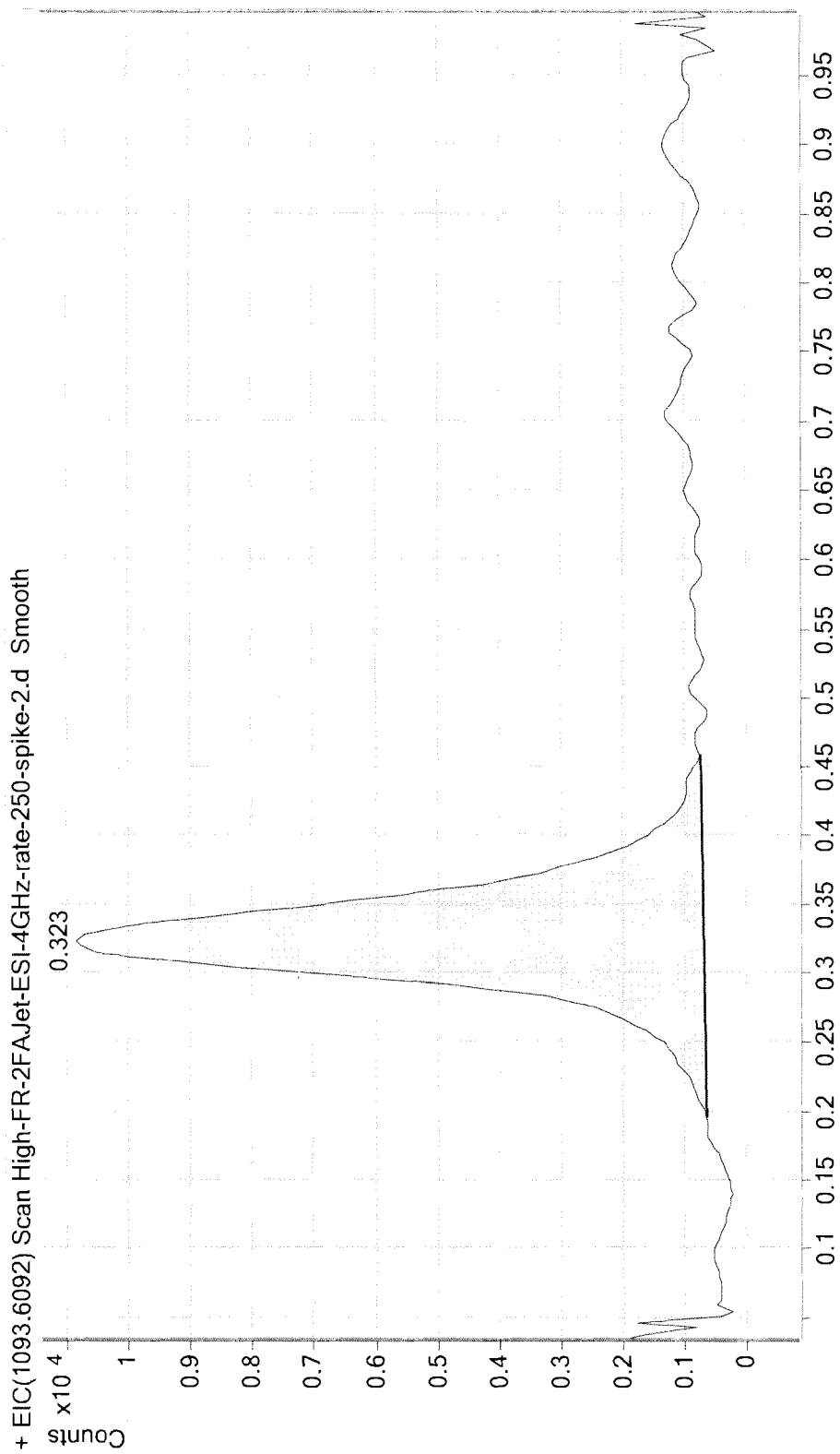
FIG. 6B shows the corresponding extracted ion chromatogram (EIC). Details are discussed in Example 3.
Figure 7A:
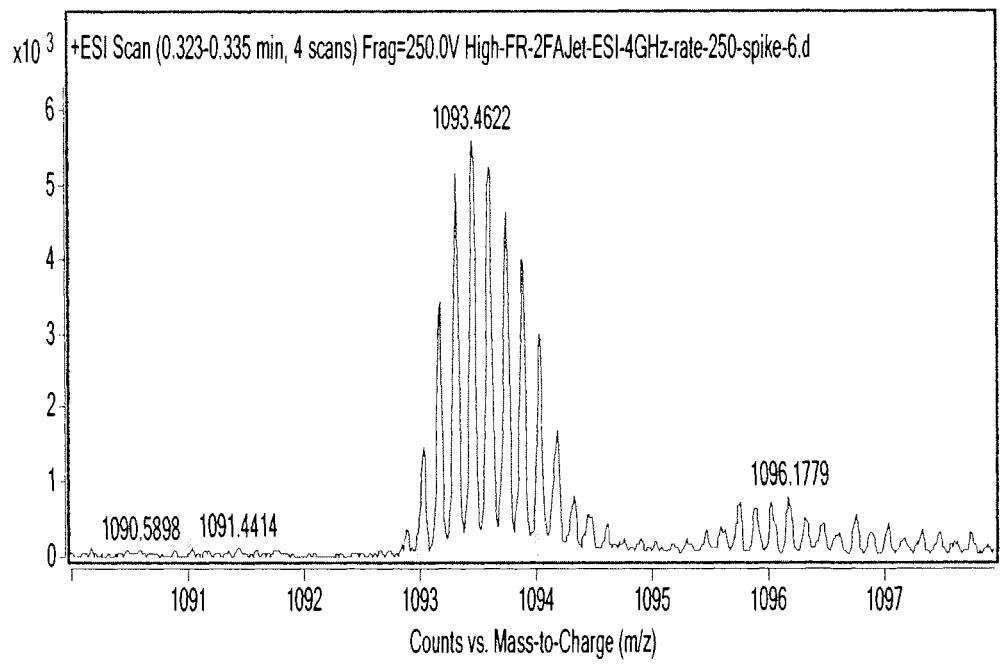
FIG. 7A shows an exemplary spectrum for about 650 fmol (on-column) intact IGF-I across a m/z range of about 1090 to 1098.
Figure 7B:
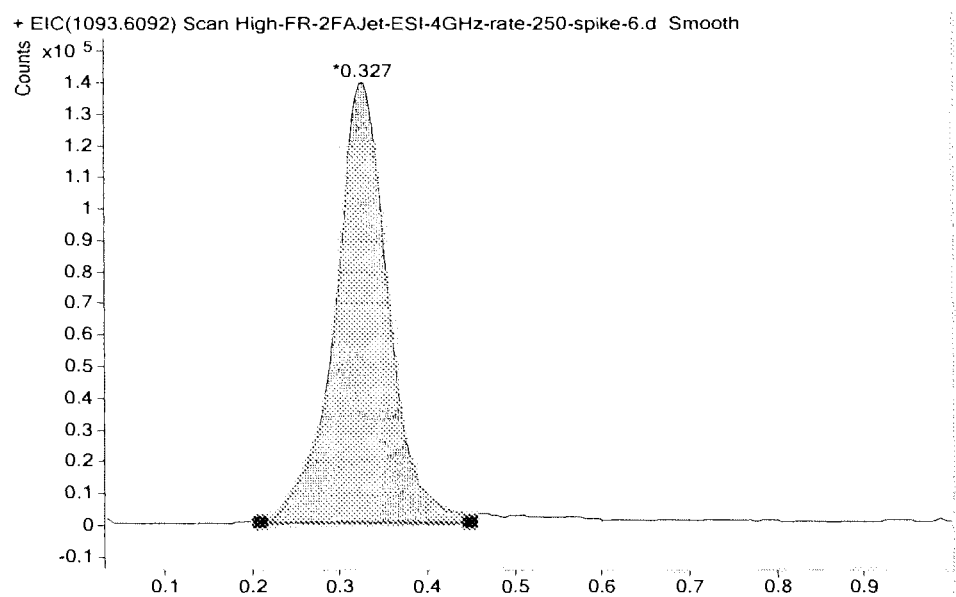
FIG. 7B shows the corresponding extracted ion chromatogram (EIC). Details are discussed in Example 3.

Exemplary spectra generated from samples at 40 fmol and 650 fmol in 100 µL blank serum across the range of m/z of about 1090 to 1098 are shown in FIGS. 6A and 7A, respectively. Extracted ion chromatograms (EICs) corresponding to the spectra shown in FIGS. 6A and 7A are presented in FIGS. 6B and 7B, respectively.

Figure 8A:
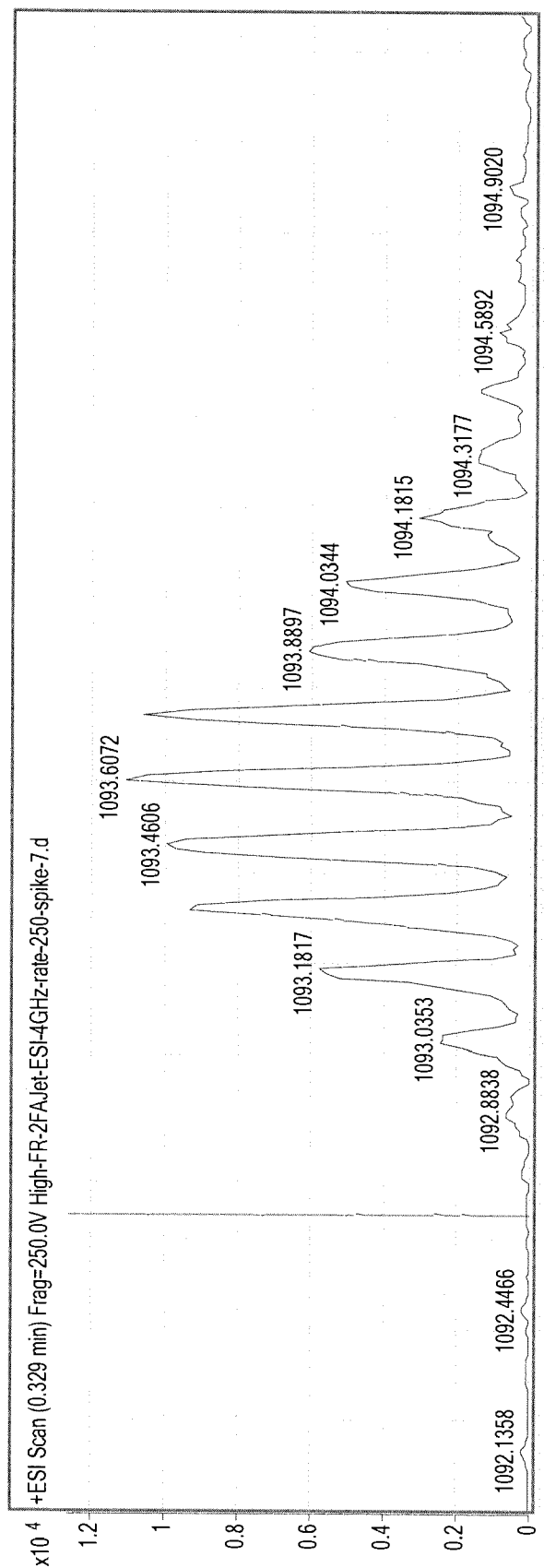
FIGS. 8A and 8B show the observed and calculated spectra of intact IGF-I across the m/z range of about 1092 to 1095.3. Details are discussed in Example 3.
Figure 8B:
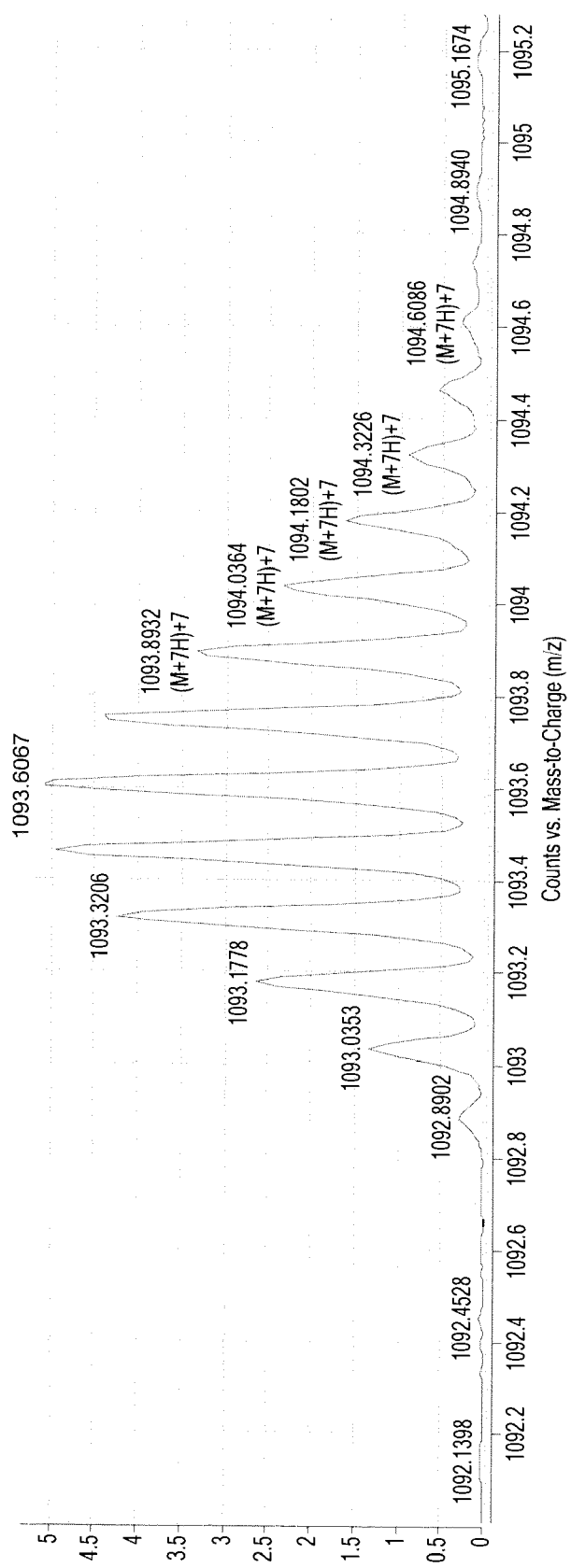

Data were collected for isotopic forms of IGF-I ions with m/z of about 1093.7±2, and the amount of intact IGF-I in the samples was qualitatively and quantitatively assessed. Qualitative assessment (i.e., confirmation of the identity of IGF-I based on the isotopic signature) was conducted by comparison of the spectra observed across the m/z range of about 1092 to 1095.3 with a calculated spectra based on naturally occurring isotopic distribution. The observed and calculated spectra are shown in FIGS. 8A and 8B, respectively.

Figure 9A:
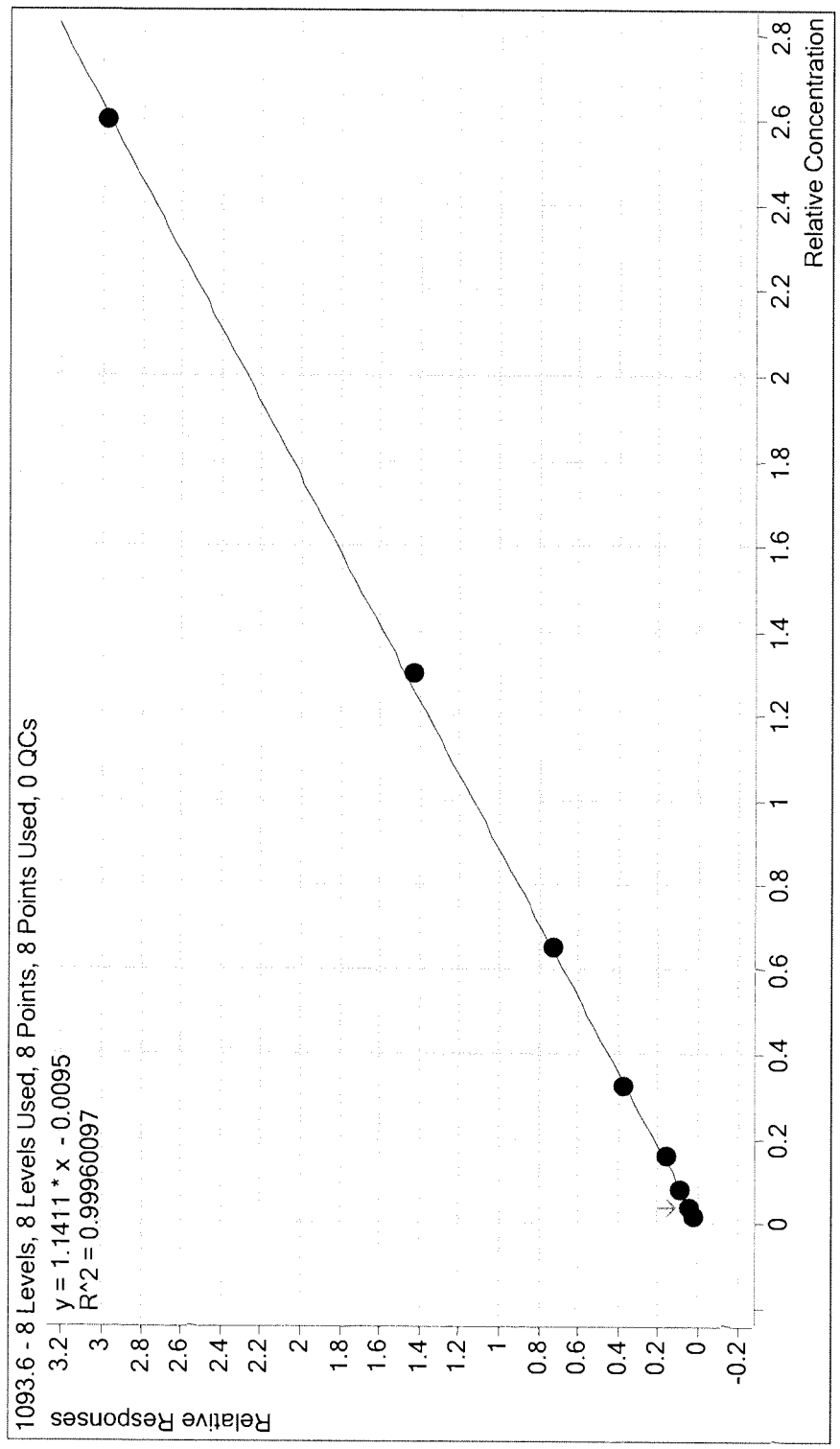
FIGS. 9A-B show plots of analytical results for various on column quantities of intact IGF-I. The full concentration range tested is depicted in FIG. 9A, with an expanded view of the low end of the concentration range depicted in FIG. 9B. Details are discussed in Example 3.
Figure 9B:
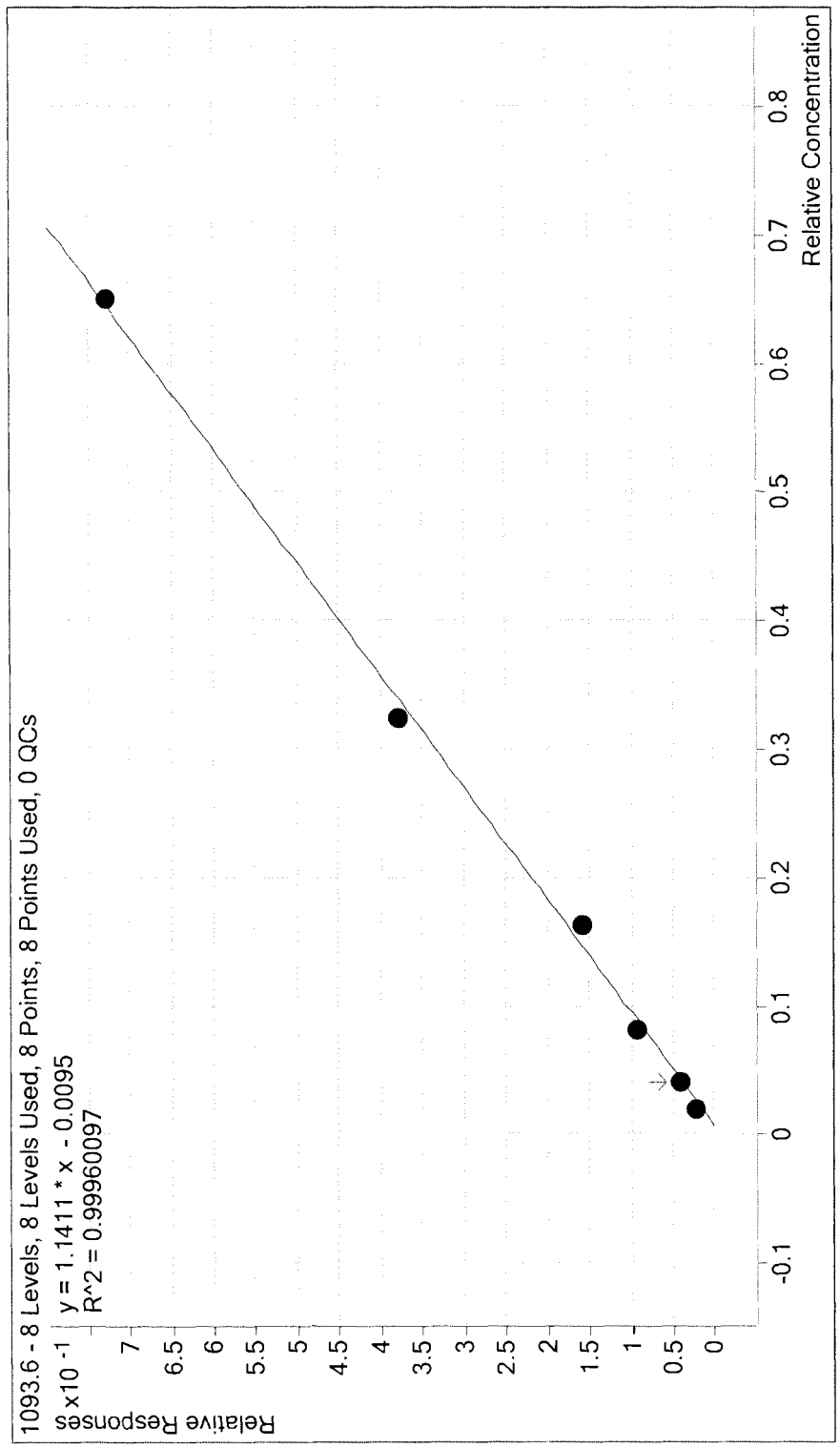

Quantitative assessment was conducted with data from a single isotopic form (corresponding to a theoretical m/z of about 1093.5209), and with summed data from multiple isotopic forms. Data from the single isotopic form was used to generate a linear calibration curve from 20 fmol to 2600 fmol intact IGF-I on column. This corresponds to observation of linearity over sample concentrations of about 8.2 ng/mL to about 1054 ng/mL (with a sample size of 100 µL). Data collected for intact IGF-I and the internal standard is presented in Table 1, below. The calibration curve is shown in FIGS. 9A (over the full concentration range tested) and 9B (expanded view of the low end of the concentration range). The goodness of fit ($R^2$) value for the intact IGF-I was 0.9996.

TABLE 1

Intact IGF-I and internal standard (intact recombinant mouse IGF-I) determination for calibration curve

| | Intact IGF-I | | | Internal Standard | |
|---|---|---|---|---|---|
| Sample Number | Actual Concentration (fmol on column) | Retention Time (min) | Ion Count | Measured Concentration (fmol on column) | Retention Time (min) | Ion Count |
| 1 | 20.3 | 0.318 | 28441 | 28.3 | 0.249 | 1246400 |
| 2 | 40.6 | 0.323 | 44032 | 45.4 | 0.251 | 1040110 |
| 3 | 81.3 | 0.312 | 87351 | 90.9 | 0.247 | 926927 |
| 4 | 162.5 | 0.330 | 137378 | 147.5 | 0.256 | 864934 |
| 5 | 325 | 0.330 | 280516 | 340.1 | 0.255 | 741062 |
| 6 | 650 | 0.327 | 525627 | 645.7 | 0.255 | 722716 |
| 7 | 1300 | 0.328 | 1142551 | 1264.0 | 0.259 | 797380 |
| 8 | 2600 | 0.325 | 2415290 | 2617.7 | 0.257 | 811149 |

Example 4: Accuracy and Precision of Quantitation of Intact IGF-I with High Resolution/High Accuracy TOF MS The intra-assay precision was generated from assaying 10 replicates from each of six QC pools (in-house QC pools and Bio-Rad Tumor Marker Controls). The three QC pools were prepared by spiking known amounts of IGF-I into stripped serum at levels of 100 ng/mL, 400 ng/mL, and 741 ng/mL. The coefficient of variation (CV) for 10 replicates of a sample was used to evaluate the reproducibility of quantitation. Data from these analyses are presented in Table 2 (for in-house QC pools) and Table 3 (for Bio-Rad Tumor Marker Controls).

TABLE 2

Intact IGF-I Intra-Assay Variation using In-House QC Pools

| Replicate | QC 1 (100 ng/mL) | QC 2 (400 ng/mL) | QC 3 (741 ng/mL) |
|---|---|---|---|
| 1 | 96.0 | 385.6 | 746.7 |
| 2 | 105.5 | 407.9 | 735.5 |
| 3 | 109.5 | 403.5 | 774.2 |
| 4 | 98.5 | 396.7 | 779.7 |
| 5 | 108.1 | 399.4 | 776.6 |
| 6 | 105.7 | 389.0 | 754.7 |
| 7 | 104.3 | 405.0 | 775.7 |
| 8 | 98.4 | 410.2 | 756.3 |
| 9 | 99.9 | 386.8 | 752.7 |
| 10 | 102.0 | 395.3 | 729.4 |
| Mean | 102.8 | 397.9 | 758.2 |
| SD | 4.51 | 8.81 | 17.89 |
| % CV | 4.4 | 2.2 | 2.4 |

TABLE 3

Intact IGF-I Intra-Assay Variation using Bio-Rad Tumor Marker Controls

| Replicate | Level 1 (Lot 19851) (ng/mL) | Level 2 (Lot 19852) (ng/mL) | Level 3 (Lot 19853) (ng/mL) |
|---|---|---|---|
| 1 | 57.8 | 245.8 | 444.2 |
| 2 | 55.5 | 243.2 | 431.7 |
| 3 | 55.0 | 248.5 | 435.4 |
| 4 | 57.5 | 248.7 | 451.1 |
| 5 | 56.1 | 245.6 | 452.7 |
| 6 | 58.6 | 248.3 | 451.3 |
| 7 | 58.5 | 247.3 | 429.7 |
| 8 | 58.0 | 234.2 | 446.6 |
| 9 | 56.6 | 241.9 | 445.5 |
| 10 | 56.9 | 244.4 | 442.7 |
| Mean | 57.1 | 244.8 | 443.1 |
| SD | 1.23 | 4.37 | 8.25 |
| % CV | 2.2 | 1.8 | 1.9 |

Statistics performed on the results of quantitation demonstrated that the reproducibility (CV) for the six QC pools ranged from 2.4% to 4.4% for spiked in-house QC pools and from 1.8% to 2.2% for Bio-Rad Tumor Marker Controls.

The inter-assay variation is defined as the reproducibility of measurements between assays. The same six QC pools as above were evaluated over 5 days. Data from these analyses are presented in Table 4 (for in-house QC pools) and Table 5 (for Bio-Rad Tumor Marker Controls).

TABLE 4

Intact IGF-I Inter-Assay Variation for In-House QC Samples

| | day 1 | day 2 | day 3 | day 4 | day 5 |
|---|---|---|---|---|---|
| In-House QC Pool 1 (100 ng/mL) | | | | | |
| run 1 | 88.5 | 96.0 | 108.3 | 109.2 | 108.5 |
| run 2 | 101.5 | 105.5 | 94.2 | 104.0 | 99.7 |
| run 3 | 98.8 | 109.5 | 105.4 | 98.8 | 106.2 |
| run 4 | 104.3 | 98.5 | 101.7 | 104.8 | 109.3 |
| run 5 | 100.8 | 108.1 | 111.9 | 111.9 | 94.7 |
| run 6 | 102.7 | 105.7 | 110.1 | 106.0 | 103.9 |
| run 7 | 106.3 | 104.3 | 100.3 | 105.1 | 105.8 |
| run 8 | 107.8 | 98.4 | 112.3 | 104.1 | 105.3 |
| Mean | 101.3 | 103.2 | 105.5 | 105.4 | 104.2 |
| SD | 6.0 | 5.0 | 6.4 | 3.9 | 4.8 |
| % CV | 5.9 | 4.8 | 6.1 | 3.7 | 4.6 |
| Accuracy | 101.3 | 103.2 | 105.5 | 105.4 | 104.2 |
| In-House QC Pool 2 (400 ng/mL) | | | | | |
| run 1 | 389.9 | 385.6 | 442.4 | 427.5 | 388.3 |
| run 2 | 398.1 | 407.9 | 441.3 | 422.8 | 394.1 |
| run 3 | 394.1 | 403.5 | 430.8 | 400.9 | 406.2 |
| run 4 | 414.6 | 396.7 | 469.0 | 448.1 | 406.7 |
| run 5 | 413.3 | 399.4 | 473.4 | 404.4 | 401.8 |
| run 6 | 405.8 | 389.0 | 405.7 | 431.0 | 411.7 |
| run 7 | 414.2 | 405.0 | 408.6 | 392.6 | 401.2 |
| run 8 | 412.4 | 410.2 | 428.5 | 423.3 | 388.3 |
| Mean | 405.3 | 399.6 | 437.5 | 418.8 | 399.8 |
| SD | 10.0 | 8.8 | 24.8 | 18.3 | 8.7 |
| % CV | 2.5 | 2.2 | 5.7 | 4.4 | 2.2 |
| Accuracy | 101.3 | 99.9 | 109.4 | 104.7 | 100.0 |
| In-House QC Pool 3 (741 ng/mL) | | | | | |
| run 1 | 755.3 | 746.7 | 826.6 | 752.2 | 734.2 |
| run 2 | 789.0 | 735.5 | 790.3 | 724.1 | 729.9 |
| run 3 | 737.2 | 774.2 | 782.6 | 757.9 | 742.3 |
| run 4 | 773.2 | 779.7 | 807.4 | 757.5 | 745.5 |
| run 5 | 778.4 | 776.6 | 763.5 | 720.2 | 747.0 |
| run 6 | 762.6 | 754.7 | 799.5 | 744.7 | 751.1 |
| run 7 | 764.9 | 775.7 | 836.9 | 747.6 | 724.1 |
| run 8 | 781.1 | 756.3 | 742.3 | 750.2 | 733.7 |
| Mean | 767.7 | 762.4 | 793.6 | 744.3 | 738.5 |
| SD | 16.5 | 16.4 | 31.3 | 14.4 | 9.4 |
| % CV | 2.1 | 2.2 | 3.9 | 1.9 | 1.3 |
| Accuracy | 103.6 | 102.9 | 107.1 | 100.5 | 99.7 |

TABLE 5

Intact IGF-I Inter-Assay Variation for Bio-Rad Tumor Marker Controls

| | day 1 | day 2 | day 3 | day 4 | day 5 |
|---|---|---|---|---|---|
| Bio-Rad Tumor Marker Control 1 | | | | | |
| run 1 | 57.8 | 54.7 | 57.9 | 57.5 | 56.6 |
| run 2 | 55.5 | 55.7 | 59.9 | 58.2 | 55.1 |
| run 3 | 55.0 | 55.5 | 60.5 | 59.3 | 57.5 |
| run 4 | 57.5 | 53.8 | 56.9 | 55.3 | 55.4 |
| run 5 | 56.1 | 53.2 | 59.1 | 58.0 | 57.8 |
| run 6 | 58.6 | 55.4 | 58.2 | 56.6 | 55.4 |
| run 7 | 58.5 | 54.9 | 61.3 | 56.9 | 55.4 |
| Mean | 57.0 | 54.7 | 59.1 | 57.4 | 56.2 |
| SD | 1.4 | 0.9 | 1.6 | 1.3 | 1.1 |
| % CV | 2.5 | 1.7 | 2.7 | 2.2 | 2.0 |
| Bio-Rad Tumor Marker Control 2 | | | | | |

TABLE 5-continued

Intact IGF-I Inter-Assay Variation for Bio-Rad Tumor Marker Controls

| | day 1 | day 2 | day 3 | day 4 | day 5 |
|---|---|---|---|---|---|
| run 1 | 245.8 | 235.6 | 258.9 | 249.7 | 250.5 |
| run 2 | 243.2 | 242.0 | 253.8 | 251.4 | 239.3 |
| run 3 | 248.5 | 243.2 | 251.5 | 239.4 | 246.2 |
| run 4 | 248.7 | 237.3 | 254.0 | 249.2 | 259.7 |
| run 5 | 245.6 | 246.6 | 257.4 | 248.6 | 258.3 |
| run 6 | 248.3 | 231.5 | 257.4 | 241.0 | 253.2 |
| run 7 | 247.3 | 235.6 | 263.7 | 240.6 | 258.0 |
| Mean | 246.8 | 238.8 | 256.7 | 245.7 | 252.2 |
| SD | 2.01 | 5.28 | 4.02 | 5.14 | 7.44 |
| % CV | 0.82 | 2.21 | 1.57 | 2.09 | 2.95 |
| Bio-Rad Tumor Marker Control 3 | | | | | |
| run 1 | 444.2 | 424.0 | 443.8 | 464.2 | 472.3 |
| run 2 | 431.7 | 448.1 | 445.1 | 457.2 | 448.7 |
| run 3 | 435.4 | 439.3 | 458.4 | 467.5 | 461.8 |
| run 4 | 451.1 | 435.1 | 470.4 | 457.2 | 438.0 |
| run 5 | 452.7 | 435.8 | 454.1 | 451.5 | 452.5 |
| run 6 | 451.3 | 428.7 | 441.9 | 447.8 | 454.4 |
| run 7 | 429.7 | 433.3 | 424.2 | 440.2 | 454.0 |
| Mean | 442.3 | 434.9 | 448.3 | 455.1 | 454.5 |
| SD | 9.91 | 7.67 | 14.58 | 9.41 | 10.65 |
| % CV | 2.24 | 1.76 | 3.25 | 2.07 | 2.34 |

Results of these measurements demonstrated that the inter-assay variation (% CV) for the pools ranged from 1.3% to 6.1% for spiked in-house QC pools and from 0.8% to 3.3% for Bio-Rad Tumor Marker Controls. The overall variation for the low, medium, and high spiked in-house QC samples was 5.0%, 5.2%, and 3.5%, respectively, while the overall variation for the low, medium, and high Bio-Rad QC material is 3.3%, 3.1%, and 2.8%, respectively.

The intra-assay accuracy is defined as the accuracy of measurements within a single assay. Each in-house QC pool was assayed in 10 replicates to determine the accuracy of repeatedly measuring intact IGF-I. The results for the QC pools yielded an accuracy of about 103%, 99%, and 102% for the three pools, respectively.

The inter-assay accuracy is defined as the accuracy of measurement between assays. The three QC pools were analyzed in seven replicates over five assays on four days to determine the accuracy of measuring intact IGF-I. The results for the analysis of the QC pools yielded an over all accuracy of 104%, 103%, and 103% for the three pools, respectively. These results are within the acceptable accuracy range of 80% to 120%.

Figure 10:
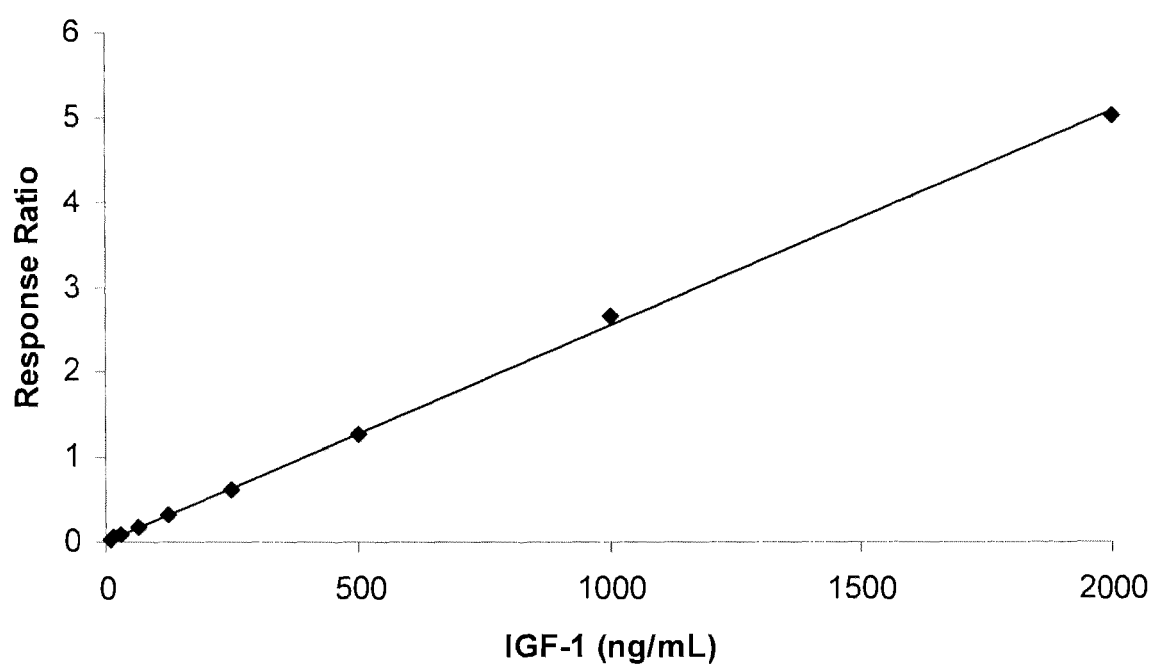
FIG. 10 shows a plot of the linearity of response for intact IGF-I at concentrations ranging from 15 ng/mL to 2000 ng/mL. Details are discussed in Example 4.

Example 4: Analyte Measurement Range for Quantitation of Intact IGF-I with High Resolution/High Accuracy TOF MS Nine stripped serum samples were prepared spiked with intact IGF-I across a concentration range of 15 ng/mL to 2000 ng/mL. These samples were then analyzed on five separate days to assess analyte detection range and linearity of detection. A weighted linear regression from five consecutive analyses yielded coefficient correlations of 0.995 or greater, with an accuracy of ±20%. Thus, the quantifiable range of the assay is at least 15 ng/mL to 2000 ng/mL. A plot of the results demonstrating linearity of response is shown in FIG. 10.

Example 5: Limit of Detection/Lower Limit of Quantitation of Intact IGF-I with High Resolution/High Accuracy TOF MS The limit of detection (LOD) is the point at which a measured value is larger than the uncertainty associated with it and is defined arbitrarily as four standard deviations (SD) from the zero concentration. A blank was measured 22 times and the resulting area ratios were back calculated to establish a LOD of 4.9 ng/mL for intact IGF-I.

The lower limit of quantitation (LLOQ) is the point at which a measured value is quantifiably meaningful. The analyte response at the LLOQ is identifiable, discrete and reproducible with a precision of better than or equal to 20% and an accuracy of between 80% and 120%. The LLOQ was determined by assaying five different samples at concentrations close to the expected LLOQ (4.9 ng/mL, 7.8 ng/mL, 15.6 ng/mL, 31.2 ng/mL, and 62.5 ng/mL) and evaluating the intra-assay reproducibility in seven runs over five days. These analyses demonstrated that the LLOQ was 15 ng/mL for intact IGF-I.

Example 6: Spike Recovery of Intact IGF-I with High Resolution/High Accuracy TOF MS A recovery study was performed by spiking patient serum with a known low level of intact IGF-I with additional intact IGF-I to achieve final concentrations of 50 ng/mL, 100 ng/mL, 400 ng/mL, and 1000 ng/mL. The spiked samples were analyzed, and the results corrected for background levels of intact IGF-I. Recoveries were calculated for each spiked concentration, with mean recoveries being about 100%, 96%, 97%, and 92%, respectively. Data from these studies are shown in Table 6.

TABLE 6

Spike recovery studies for intact IGF-I in patient serum

| sample | Spike Amount | | | |
|---|---|---|---|---|
| | 50 ng/mL % recovery | 100 ng/mL % recovery | 400 ng/mL % recovery | 1000 ng/mL % recovery |
| 1 | 92.6 | 95.2 | 96.4 | 97.7 |
| 2 | 88.3 | 102.3 | 96.7 | 89.9 |
| 3 | 118 | 91.0 | 98.2 | 89.0 |
| average | 99.8 | 96.1 | 97.1 | 92.2 |

Example 7: Inter-Method Correlation for Quantitation of Intact IGF-I

Samples from 100 patients were split and analyzed with the LC-MS method described above. Portions of the samples were also assayed using the Siemens IMMULITE 2000 immunoassay system (Siemens Healthcare Diagnostics, Inc.), the Meso Scale Discovery SECTOR system (Meso Scale Discovery), and RIA methods (conducted by Esoterix, Inc., Test Code 500282, Blocking RIA after acid:alcohol extraction). Of the 100 split samples, 60 were analyzed with the IMMULITE system.

Data from the four methods were analyzed by Deming regression. Results of the comparisons are shown in Table 7. The LC-MS analysis was demonstrated to have the best agreement with the RIA method.

TABLE 7

Deming regression analysis of comparison of four intact IGF-I assay methods

| Methods Compared | n | Variable | | |
|---|---|---|---|---|
| | | m | b | Sy.x |
| LC-MS vs RIA | 100 | 1.039 ± 0.01572 | −11.55 ± 5.673 | 36.1 |
| LC-MS vs IMMULITE | 60 | 0.8320 ± 0.02363 | 43.78 ± 11.49 | 63.1 |
| LC-MS vs MSD | 100 | 0.8310 ± 0.03174 | 46.12 ± 12.60 | 86.6 |

Example 8: Intact IGF-I Interference Studies

The effects of hemolysis on intact IGF-I determination were evaluated by titrating lysed red blood cells into patient serum to establish estimated hemoglobin concentrations of 0 mg/mL, 2.5 mg/mL, 5 mg/mL, 7.5 mg/mL, 10 mg/mL, and 20 mg/mL. Three different patient samples were titrated as described and extracted for intact IGF-I analysis. The results were compared to the non-spiked pool results and the percent difference was calculated. Data generated for this comparison is presented in Table 8.

TABLE 8

Hemolytic interference studies for intact IGF-I in patient serum samples
% Recovery Compared to Control

| | Hemoglobin Concentration (mg/mL) | | | | | |
|---|---|---|---|---|---|---|
| | 0 | 2.5 | 5 | 7.5 | 10 | 20 |
| sample 1 | 100.0 | 100.7 | 99.0 | 105.4 | 101.0 | 103.7 |
| sample 2 | 100.0 | 100.5 | 99.8 | 104.7 | 100.5 | 98.3 |
| sample 3 | 100.0 | 98.0 | 105.1 | 110.7 | 104.1 | 107.1 |

As seen in Table 8, all whole blood spiked samples yielded acceptable results (80%-120% of control value) and demonstrated no dependence between intact IGF-I detection and hemoglobin concentration. Therefore, samples showing light to moderate hemolysis are acceptable.

The effects of lipemia on intact IGF-I determination were evaluated by titrating brain lipid extract into patient serum to establish estimated lipid concentrations of 0 mg/mL, 2.5 mg/mL, 5 mg/mL, 7.5 mg/mL, 10 mg/mL, and 20 mg/mL. Three different patient samples were titrated as described and extracted for IGF-I analysis. The results were compared to the non-spiked pool results and the percent difference was calculated. Data generated for this comparison is presented in Table 9.

TABLE 9

Lipemic interference studies for intact IGF-I in patient serum samples
% Recovery Compared to Control

| | Lipid Concentration (mg/mL) | | | | | |
|---|---|---|---|---|---|---|
| | 0 | 2.5 | 5 | 7.5 | 10 | 20 |
| sample 1 | 100.0 | 109.3 | 107.6 | 113.1 | 104.1 | 106.6 |
| sample 2 | 100.0 | 105.9 | 93.7 | 91.2 | 105.9 | 96.2 |
| sample 3 | 100.0 | 103.3 | 102.6 | 101.7 | 94.4 | 112.6 |

As seen in Table 9, all lipid spiked samples yielded acceptable results (80%-120% of control value) and demonstrated no dependence between intact IGF-I detection and lipid concentration. Therefore, samples showing light to moderate lipemia are acceptable.

The effects of bilirubin on intact IGF-I determination were evaluated by titrating bilirubin into patient serum to establish estimated bilirubin concentrations of 0 mg/mL, 0.25 mg/mL, 0.5 mg/mL, 0.75 mg/mL, 1 mg/mL, and 2 mg/mL. Three different patient samples were titrated as described and extracted for intact IGF-I analysis. The results were compared to the non-spiked pool results and the percent difference was calculated. Data generated for this comparison is presented in Table 10.

TABLE 10

Bilirubin interference studies for intact
IGF-I in patient serum samples
% Recovery Compared to Control

| | Bilirubin Concentration (mg/mL) | | | | |
|---|---|---|---|---|---|
| | 0 | 0.25 | 0.5 | 0.75 | 1 | 2 |
| sample 1 | 100.0 | 84.3 | 91.4 | 97.9 | 89.3 | 94.3 |
| sample 2 | 100.0 | 87.5 | 96.5 | 88.5 | 90.5 | 104.0 |
| sample 3 | 100.0 | 90.9 | 90.6 | 94.1 | 97.6 | 98.6 |

As seen in Table 10, all bilirubin spiked samples yielded acceptable results (80%-120% of control value) and demonstrated no dependence between intact IGF-I detection and bilirubin concentration. Therefore, samples showing light to moderate bilirubin are acceptable.

The effects of IGFBP-3 on intact IGF-I determination were evaluated by titrating recombinant IGFBP-3 into patient serum to establish estimated IGFBP-3 concentrations of 0 mg/L, 2 mg/L, 5 mg/L, 8 mg/L, and 9 mg/L. Three different patient samples were titrated as described and extracted for intact IGF-I analysis within three hours of their preparation. Another set of 15 patient samples were spiked with IGFBP-3 to a final concentration of 5 mg/L and equilibrated for three days at 4° C. before extraction. In both experiments, the results were compared to the non-spiked pool results and the percent difference was calculated. Data generated for these comparisons are presented in Tables 11 and 12, respectively.

TABLE 11

IGFBP-3 interference studies for intact IGF-I in patient
serum samples (extracted 3 hours after preparation)
% Recovery Compared to Control

| | IGFBP-3 Concentration (mg/L) | | | |
|---|---|---|---|---|
| | 2 | 5 | 8 | 9 |
| Sample 1 | 80 | 94 | 92 | 106 |
| Sample 2 | 111 | 102 | 104 | 101 |
| Sample 3 | 99 | 109 | 119 | 98 |

TABLE 12

IGFBP-3 interference studies for intact IGF-I in patient
serum samples (extracted 3 days after preparation)

| Sample | % Recovery Compared to Control (5 mg/L IGFBP-3) |
|---|---|
| 1 | 96.7 |
| 2 | 111.7 |
| 3 | 117.0 |

TABLE 12-continued

IGFBP-3 interference studies for intact IGF-I in patient
serum samples (extracted 3 days after preparation)

| Sample | % Recovery Compared to Control (5 mg/L IGFBP-3) |
|---|---|
| 4 | 116.2 |
| 5 | 105.9 |
| 6 | 115.2 |
| 7 | 100.6 |
| 8 | 102.3 |
| 9 | 104.6 |
| 10 | 113.4 |
| 11 | 99.9 |
| 12 | 109.8 |
| 13 | 94.2 |
| 14 | 109.7 |
| 15 | 90.4 |
| Mean | 105% |

As seen in Tables 11 and 12, all IGFBP-3 spiked samples yielded acceptable results (80%-120% of control value) and demonstrated no dependence between intact IGF-I detection and IGFBP-3 concentration. Therefore, IGFBP-3 does not appear to interfere with the analysis of IGF-I.

Example 9: IGF-I Sample Type Studies

Ten patient pools were collected in four Vacutainer® types: serum, citrate plasma, heparin plasma, and EDTA plasma. Levels of intact IGF-I were determined in samples from each sample type. A pairwise analysis of variance (ANOVA) only indicated statistically significant differences between serum and citrate plasma. This indicates that serum, heparin plasma, and EDTA plasma are acceptable sample types. Data from these studies are found in Table 13.

TABLE 13

Effect of Sample Type on IGF-I Quantitation
Intact IGF-I (measured value)

| Patient | Serum | EDTA plasma | Heparin Plasma | Citrate Plasma |
|---|---|---|---|---|
| 1 | 231.3 | 215.9 | 234.1 | 189.1 |
| 2 | 244.9 | 216.0 | 219.3 | 209.8 |
| 3 | 451.9 | 470.5 | 486.0 | 376.6 |
| 4 | 289.4 | 252.3 | 264.3 | 232.7 |
| 5 | 545.4 | 491.3 | 540.4 | 465.9 |
| 6 | 213.1 | 208.7 | 200.5 | 179.7 |
| 7 | 344.5 | 315.7 | 337.7 | 288.5 |
| 8 | 168.7 | 176.5 | 172.3 | 147.9 |
| 9 | 125.4 | 112.3 | 116.2 | 108.3 |
| 10 | 217.9 | 210.7 | 209.1 | 173.6 |
| p value (compared to serum) | n/a | p > 0.05 | p > 0.05 | p < 0.001 |

Example 10: Enrichment of IGF-II Proteins or Fragments

Intact human IGF-II was extracted from calibration, QC, and patient serum samples using a combination of off-line sample preparation and subsequent on-line SPE and HPLC. Acid ethanol extraction was conducted as follows.

100 µL of each sample was treated with 400 µL of acid/ethanol (87.5% Etoh/12.5% 2M HCl) to form a precipitate. The mixture was subject to centrifugation to obtain a supernatant and pellet. 350 µL of supernatant was then withdrawn, mixed with 60 µL 1.5M Tris base, and incubated at −20° C. for 1 hour. The incubated mixture was then subjected to centrifugation and any precipitate that formed with the addition of the Tris base was discarded. The supernatant is then applied directly onto an HPLC column for mass spectrometric analysis.

After the above sample preparation, the resulting solutions were injected into a Cohesive LC system for on-line SPE and HPLC processing prior to mass spectrometric analysis. On-line extraction and enrichment of intact human IGF-II was accomplished using a Phenomenex Monolithic Onyx C18 Guard Cartridge (10×4.6 mm) as an on-line SPE column. Analytical separation was accomplished by HPLC with a Phenomenex Onyx Monolithic C18 column (50×2.0 mm).

Example 11: Detection and Quantitation of Intact IGF-II with High Resolution/High Accuracy TOF MS MS was performed using an Agilent 6530 Accurate-Mass Q-TOF MS system (Agilent Technologies, Inc.). This system employs a high resolution/high accuracy TOF MS analyzer capable of high resolution/high accuracy MS. The instrument exhibited resolving power of approximately 21,000 FWHM, and mass accuracy of approximately 3 ppm while measuring intact IGF-II. The following software was used for these experiments: Agilent MassHunter Workstation Acquisition B.02.01; Agilent MassHunter Quantitative Software B.03.02; Agilent MassHunter Qualitative software B.02.00; and Cohesive Aria OS v.1.5.1.

Figure 11:
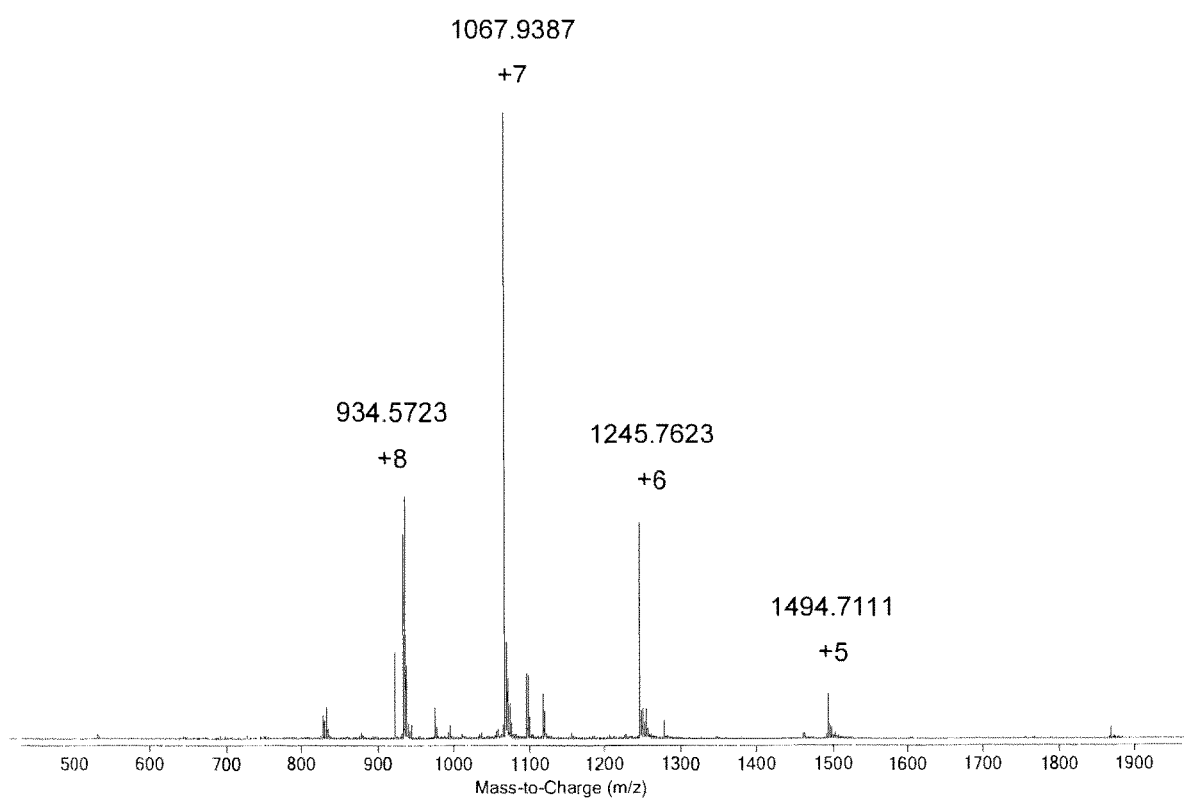
FIG. 11 shows an exemplary spectrum across a m/z range of about 500 to 1900 for intact IGF-II generated with a high resolution/high accuracy TOF mass spectrometer. Details are discussed in Example 11.

An exemplary spectrum generated from high resolution/high accuracy mass spectrometric analysis of intact human IGF-II demonstrating intact IGF-II ions in charge states of 8+, 7+, 6+, and 5+ is shown in FIG. 11. This spectrum was collected across the range of m/z of about 400 to 2000. As shown in FIG. 11, peaks from different charge states are seen at m/z of about 934.57, 1067.94, 1245.76, and 1494.71.

An exemplary spectrum generated from high resolution/high accuracy mass spectrometric analysis of intact human IGF-II demonstrating intact IGF-II ions in a 7+ charge state is shown in FIG. 12. This spectrum was collected across the range of m/z of about 1066 to 1070. As shown in FIG. 12, peaks from naturally occurring isotopes are seen at m/z ratios of about 1067.36, 1067.51, 1067.65, 1067.80, 1067.94, 1068.08, 1068.23, 1068.37, 1068.51, 1068.65, 1068.80, 1068.94, and 1068.08.

Data was collected for two isotopic forms of intact human IGF-II ions with m/z of about 1067.94 and 1068.08, and the amount of intact human IGF-II in the samples was qualitatively and quantitatively assessed. Qualitative assessment (i.e., confirmation of the identity of IGF-II based on the isotopic signature) was conducted by comparison of the experimental isotopic ratio of the peaks at 106.94 and 1068.08 with a theoretical ratio calculated from naturally occurring isotopic distribution.

Figure 13:
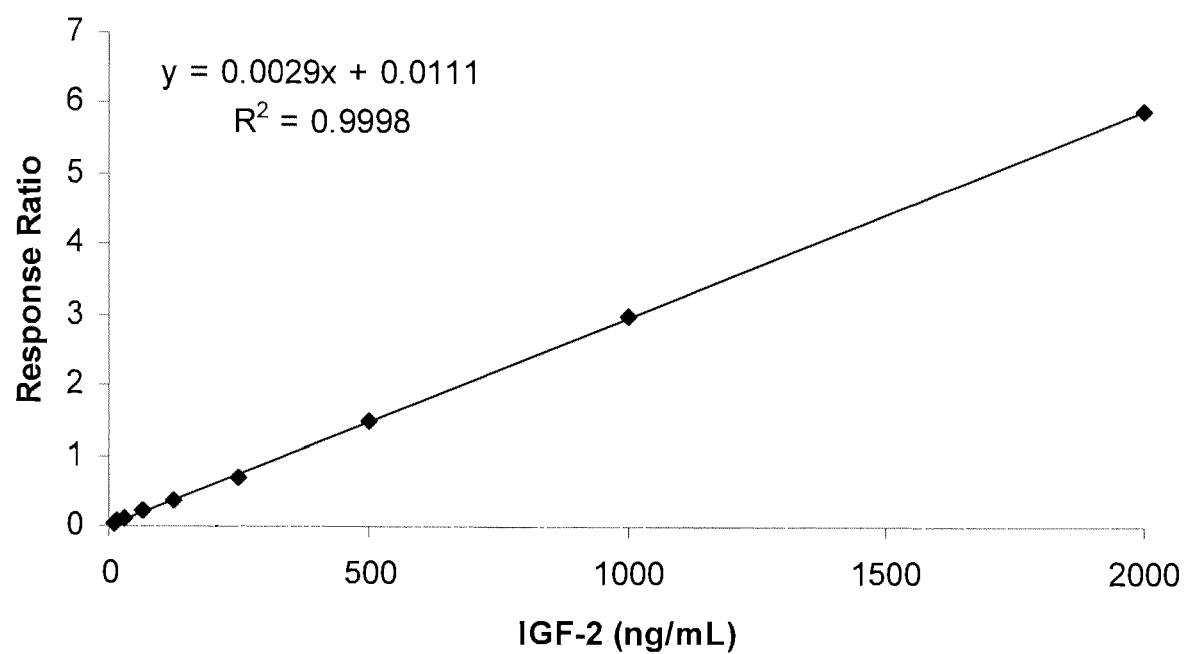
FIG. 13 shows a plot of the linearity of response for intact IGF-II at concentrations ranging from 15 ng/mL to 2000 ng/mL. Details are discussed in Example 11.
Figure 14:
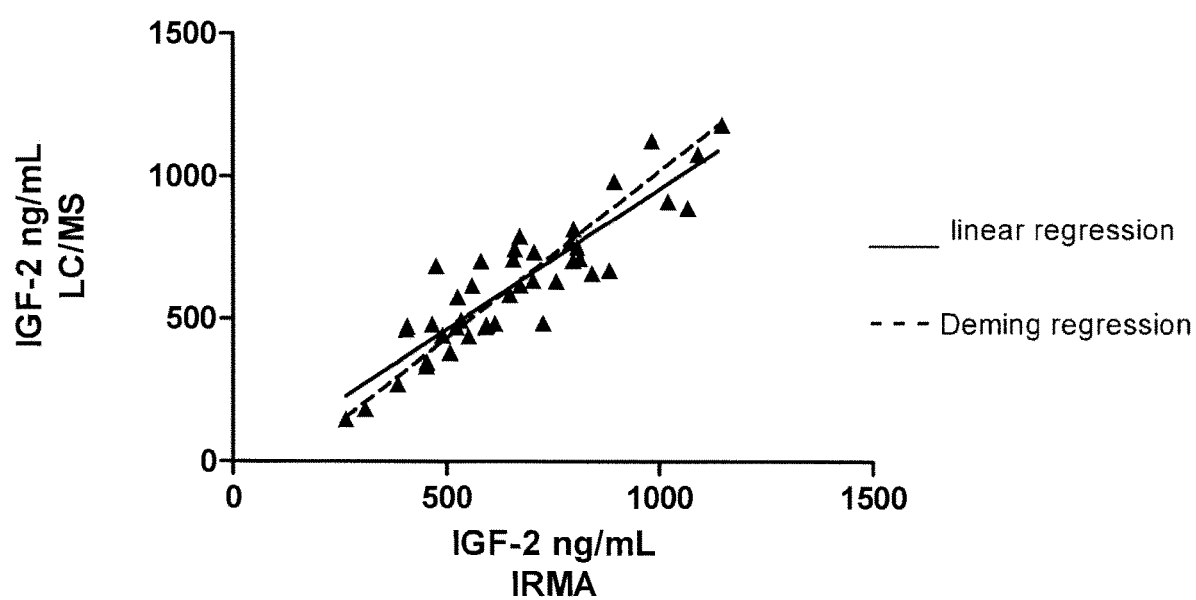
FIG. 14 shows comparison of analytical results for quantitation of intact IGF-II by the instant LC-MS methods versus analysis by IRMA. Details are discussed in Example 15.

Quantitative assessment was conducted with the sum of the two isotopic forms indicated above. A linear calibration curve was generated for calibrator pool concentrations of about 15 ng/mL to about 2000 ng/mL intact human IGF-II. Data collected for intact human IGF-II is presented in Table 14, below. The calibration curve is shown in FIG. 13 over the full concentration range tested. The goodness of fit ($R^2$) value for the intact human IGF-II was 0.9998.

TABLE 14

Intact human IGF-II determination for calibration curve

| | Intact human IGF-II | | |
|---|---|---|---|
| Sample Number | Actual Concentration (ng/mL) | Measured Concentration (ng/mL) | Accuracy (%) |
| 1 | 7.81 | 6.5 | 82.9 |
| 2 | 15.63 | 17.3 | 110.9 |
| 3 | 31.25 | 35.0 | 112.0 |
| 4 | 62.50 | 67.2 | 107.5 |
| 5 | 125.00 | 112.9 | 90.3 |
| 6 | 250.00 | 2335.9 | 94.4 |
| 7 | 500.00 | 502.4 | 100.5 |
| 8 | 1000.00 | 1014.7 | 101.5 |
| 9 | 2000.00 | 2000.3 | 100.0 |

Example 12: Accuracy and Precision of Quantitation of Intact IGF-II with High Resolution/High Accuracy TOF MS The intra-assay precision was generated from assaying 8 replicates from each of 6 QC pools (3 in-house QC pools and 3 off-the-clot human serum samples). The coefficient of variation (CV) for 8 replicates of a sample was used to evaluate the reproducibility of quantitation. Data from these analyses are presented in Table 15 (for in-house QC pools) and Table 16 (for off-the-clot human serum samples).

TABLE 15

Intact IGF-II Intra-Assay Variation using In-House QC Pools

| Replicate | QC 1 (200 ng/mL) | QC 2 (500 ng/mL) | QC 3 (1200 ng/mL) |
|---|---|---|---|
| 1 | 193.6 | 497.0 | 1214.7 |
| 2 | 189.8 | 504.1 | 1205.9 |
| 3 | 197.4 | 504.1 | 1158.1 |
| 4 | 195.0 | 528.3 | 1197.2 |
| 5 | 215.6 | 499.5 | 1205.3 |
| 6 | 200.5 | 498.9 | 1183.5 |
| 7 | 213.7 | 502.0 | 1231.7 |
| 8 | 205.3 | 494.0 | 1242.9 |
| Mean | 201.4 | 503.5 | 1204.9 |
| SD | 9.4 | 10.6 | 26.6 |
| % CV | 4.7 | 2.1 | 2.2 |
| Accuracy | 100.7 | 100.7 | 100.4 |

TABLE 16

Intact IGF-II Intra-Assay Variation using Off-the-Clot Human Serum Samples

| Replicate | Level 1 (ng/mL) | Level 2 (ng/mL) | Level 3 (ng/mL) |
|---|---|---|---|
| 1 | 43.7 | 224.6 | 446.6 |
| 2 | 44.9 | 237.9 | 441.1 |
| 3 | 36.9 | 224.4 | 452.4 |
| 4 | 38.9 | 233.6 | 448.7 |
| 5 | 40.2 | 212.8 | 466.4 |
| 6 | 39.5 | 233.7 | 441.1 |
| 7 | 35.8 | 225.4 | 445.5 |
| 8 | 41.2 | 220.2 | 460.4 |
| Mean | 40.1 | 226.6 | 450.3 |
| SD | 3.1 | 8.2 | 9.1 |
| % CV | 7.7 | 3.6 | 2.0 |

Statistics performed on the results of quantitation demonstrated that the reproducibility (CV) for the six QC pools ranged from 2.1% to 4.7% for spiked in-house QC pools and from 2.0% to 7.7% for off-the-clot human serum samples.

The intra-assay accuracy is defined as the accuracy of measurements within a single assay. The repeated measurement of intact human IGF-II in the in-house QC pools yielded accuracies of about 100.7%, 100.7%, and 100.4% for pools at 200 ng/mL, 500 ng/mL, and 1200 ng/mL, respectively.

The inter-assay variation is defined as the reproducibility of measurements between assays. The same 6 QC pools as above were evaluated over 5 days. Data from these analyses are presented in Table 17 (for in-house QC pools) and Table 18 (for off-the-clot human serum samples).

TABLE 17

Intact IGF-II Inter-Assay Variation for In-House QC Samples.

|  | day 1 | day 2 | day 3 | day 4 | day 5 |
| --- | --- | --- | --- | --- | --- |
| In-House QC Pool 1 (200 ng/mL) | | | | | |
| run 1 | 193.6 | 208.7 | 196.7 | 235.3 | 196.1 |
| run 2 | 189.8 | 216.4 | 210.8 | 224.9 | 199.4 |
| run 3 | 197.4 | 198.3 | 187.1 | 209.5 | 198.3 |
| run 4 | 195.0 | 210.3 | 191.8 | 230.0 | 194.4 |
| run 5 | 215.6 | 197.3 | 196.8 | 200.9 | 198.1 |
| run 6 | 200.5 | 223.5 | 191.2 | — | 201.8 |
| run 7 | 213.7 | 204.2 | 185.9 | 218.5 | 196.0 |
| run 8 | 205.3 | — | 192.0 | 224.2 | 198.7 |
| Mean | 201.4 | 208.4 | 194.1 | 220.5 | 197.9 |
| SD | 9.4 | 9.5 | 7.8 | 11.9 | 2.3 |
| % CV | 4.7 | 4.5 | 4.0 | 5.4 | 1.2 |
| Accuracy | 100.7 | 104.2 | 97.0 | 110.2 | 98.9 |
| In-House QC Pool 2 (500 ng/mL) | | | | | |
| run 1 | 497.0 | 494.2 | 523.9 | 494.5 | 457.9 |
| run 2 | 504.1 | — | 496.2 | 491.5 | 499.1 |
| run 3 | 504.1 | 498.3 | 514.5 | 502.9 | 471.7 |
| run 4 | 528.3 | 482.3 | 468.5 | 491.5 | 500.2 |
| run 5 | 499.5 | 505.5 | 496.8 | 490.1 | 493.3 |
| run 6 | 498.9 | 475.8 | 476.6 | 529.8 | 501.7 |
| run 7 | 502.0 | 464.7 | 506.9 | 492.9 | 486.4 |
| run 8 | 494.0 | 489.3 | 513.8 | 484.9 | 507.0 |
| Mean | 503.5 | 487.2 | 499.6 | 497.3 | 489.7 |
| SD | 10.6 | 14.1 | 19.2 | 14.1 | 16.9 |
| % CV | 2.1 | 2.9 | 3.8 | 2.8 | 3.5 |
| Accuracy | 100.7 | 97.4 | 99.9 | 99.5 | 97.9 |
| In-House QC Pool 3 (1200 ng/mL) | | | | | |
| run 1 | 1214.7 | 1155.8 | 1201.9 | 1287.5 | 1188.8 |
| run 2 | 1205.9 | 1218.0 | 1116.1 | 1281.5 | 1262.6 |
| run 3 | 1158.1 | 1141.0 | 1202.9 | 1104.4 | 1165.1 |
| run 4 | 1197.2 | 1110.8 | 1106.8 | 1327.7 | 1168.8 |
| run 5 | 1205.3 | 1055.3 | 1248.1 | 1265.9 | 1146.5 |
| run 6 | 1183.5 | 1221.2 | 1184.0 | 1207.0 | 1250.2 |
| run 7 | 1231.7 | 1233.4 | 1290.4 | 1158.0 | 1062.2 |
| run 8 | 1242.9 | 1088.1 | 1191.7 | 1152.8 | 1151.9 |
| Mean | 1204.9 | 1153.0 | 1192.7 | 1223.1 | 1174.5 |
| SD | 26.6 | 66.6 | 61.1 | 79.1 | 62.9 |
| % CV | 2.2 | 5.8 | 5.1 | 6.5 | 5.4 |
| Accuracy | 100.4 | 96.1 | 99.4 | 101.9 | 97.9 |

TABLE 18

Intact IGF-II Inter-Assay Variation for Off-the-Clot Human Serum Samples.

|  | day 1 | day 2 | day 3 | day 4 | day 5 |
| --- | --- | --- | --- | --- | --- |
| Off-the-Clot Human Serum Sample 1 | | | | | |
| run 1 | 43.7 | 43.5 | 40.1 | 44.8 | 42.8 |
| run 2 | 44.9 | 37.7 | 43.0 | 43.9 | 44.0 |
| run 3 | 36.9 | 43.1 | 43.7 | 44.7 | 43.5 |
| run 4 | 38.9 | 40.2 | 39.6 | 42.5 | 40.9 |
| run 5 | 40.2 | 42.9 | 40.8 | 42.9 | 42.4 |
| run 6 | 39.5 | 38.2 | 41.5 | 41.6 | 43.6 |
| run 7 | 35.8 | 36.4 | 38.3 | 42.3 | 41.7 |
| run 8 | 41.2 | 34.3 | 37.7 | 39.7 | 42.9 |
| Mean | 40.1 | 39.5 | 40.6 | 42.8 | 42.7 |
| SD | 3.1 | 3.4 | 2.1 | 1.7 | 1.0 |
| % CV | 7.7 | 8.7 | 5.2 | 3.9 | 2.4 |
| Off-the-Clot Human Serum Sample 2 | | | | | |
| run 1 | 224.6 | 222.4 | 228.8 | 216.3 | 228.2 |
| run 2 | 237.9 | 227.8 | 222.9 | 214.6 | 226.4 |
| run 3 | 224.4 | 217.2 | 236.4 | 222.8 | 222.4 |
| run 4 | 233.6 | 224.5 | 217.5 | 214.4 | 235.4 |
| run 5 | 212.8 | 222.1 | 244.2 | 226.4 | 219.2 |
| run 6 | 233.7 | 229.7 | 223.8 | 220.4 | 222.7 |
| run 7 | 225.4 | 233.7 | 225.6 | 213.3 | 211.3 |
| run 8 | 220.2 | 220.5 | 230.2 | 210.9 | 235.7 |
| Mean | 226.6 | 224.7 | 228.7 | 217.4 | 225.2 |
| SD | 8.2 | 5.4 | 8.4 | 5.3 | 8.2 |
| % CV | 3.6 | 2.4 | 3.7 | 2.4 | 3.6 |
| Off-the-Clot Human Serum Sample 3 | | | | | |
| run 1 | 446.6 | 446.5 | 453.6 | 454.4 | 448.5 |
| run 2 | 441.1 | 454.3 | 439.5 | 456.5 | 450.4 |
| run 3 | 452.4 | 469.6 | 453.8 | 450.2 | 442.3 |
| run 4 | 448.7 | 452.9 | 453.3 | 456.8 | 434.3 |
| run 5 | 466.4 | 464.5 | 461.0 | 460.8 | 458.1 |
| run 6 | 441.1 | 442.3 | 441.2 | 461.2 | 444.6 |
| run 7 | 445.5 | 454.5 | 443.4 | 450.5 | 457.9 |
| run 8 | 460.4 | 469.4 | 441.1 | 430.2 | 450.6 |
| Mean | 450.3 | 456.8 | 448.4 | 452.6 | 448.3 |
| SD | 9.1 | 10.2 | 8.0 | 9.9 | 8.0 |
| % CV | 2.0 | 2.2 | 1.8 | 2.2 | 1.8 |

Results of these measurements demonstrated that the inter-assay variation (% CV) for the pools ranged from 3.2% to 6.1% for spiked in-house QC pools and from 2.0% to 6.5% for off-the-clot human serum samples.

The inter-assay accuracy is defined as the accuracy of measurement between assays. The repeated measurement of intact human IGF-II in the in-house QC pools yielded accuracies of about 102.2%, 99.1%, and 99.1% for the pools at 200 ng/mL, 500 ng/mL, and 1200 ng/mL, respectively. These results are within the acceptable accuracy range of 80% to 120%.

Example 13: Limit of Detection/Lower Limit of Quantitation of Intact IGF-II with High Resolution/High Accuracy TOF MS The limit of blank (LOB) is the point at which a measured value is larger than the uncertainty associated with it and is defined arbitrarily as 2 standard deviations (SD) from the zero concentration. Blank samples of the appropriate biological matrix (stripped serum) were obtained and measured 15 times. The resulting area ratios were back calculated to establish a LOB of 4.9 ng/mL of intact human IGF-II in stripped serum.

The limit of detection (LOD) is the point at which a measured value is larger than the uncertainty associated with it and is defined arbitrarily as four standard deviations (SD) from the zero concentration. A blank was measured 15 times and the resulting area ratios were back calculated to establish a LOD of 8.2 ng/mL for intact human IGF-II.

The lower limit of quantitation (LLOQ) is the point at which a measured value is quantifiably meaningful. The analyte response at the LLOQ is identifiable, discrete and reproducible with a precision of better than or equal to 20% and an accuracy of between 80% and 120%. The LLOQ was determined by assaying five different samples at concentrations close to the expected LLOQ (4.9 ng/mL, 7.8 ng/mL, 15.6 ng/mL, 31.2 ng/mL, and 62.5 ng/mL) and evaluating the intra-assay reproducibility in six runs over five days. These analyses demonstrated that the LLOQ was 30 ng/mL for intact human IGF-II.

Example 14: Spike Recovery of Intact IGF-II with High Resolution/High Accuracy TOF MS A recovery study was performed by spiking stripped serum with intact human IGF-II to achieve final concentrations of 62.5 ng/mL, 125 ng/mL, 500 ng/mL, and 1200 ng/mL. The spiked samples were analyzed, and the results corrected for background levels of intact human IGF-II. Recoveries were calculated for each spiked concentration, with mean recoveries being about 106%, 104%, 99%, and 99%, respectively. Data from these studies are shown in Table 19.

TABLE 19

Spike recovery studies for intact IGF-II in patient serum

| | Spike Amount | | | |
|---|---|---|---|---|
| sample | 62.5 ng/mL % recovery | 125 ng/mL % recovery | 500 ng/mL % recovery | 1200 ng/mL % recovery |
| 1 | 99.1 | 101.1 | 100.7 | 100.4 |
| 2 | 101.9 | 101.4 | 97.4 | 96.1 |
| 3 | 116.7 | 109.5 | 99.9 | 99.4 |
| average | 105.9 | 104.0 | 99.3 | 98.6 |

Example 15: Inter-Method Correlation for Quantitation of Intact IGF-II

Samples from 42 patients were split and analyzed with the LC-MS method described above. Portions of the samples were also assayed using an IRMA methodology performed by Quest Diagnostics Nichols Institute.

Data from the two methods were analyzed by linear and Deming regression. Results of the comparisons are shown in Table 20 and FIG. 13. The LC-MS analysis was demonstrated to have good agreement with the IRMA method.

TABLE 20

Comparison of LC-MS and IRMA assay methods for intact IGF-II

| IGF-II by LC-MS vs IRMA | Variable | | | |
|---|---|---|---|---|
| Comparison | n | m | b | $R^2$ |
| Linear regression | 42 | 0.9829 ± 0.07627 | −28.10 ± 53.02 | 0.82 |
| Deming regression | 42 | 1.171 ± 0.09090 | −153.0 ± 63.19 | n/a |

Example 16: IGF-II Interference Studies

The effects of hemolysis on intact human IGF-II determination were evaluated by titrating lysed red blood cells into patient serum to establish estimated hemoglobin concentrations of 0 mg/mL, 2.5 mg/mL, 5 mg/mL, 7.5 mg/mL, 10 mg/mL, and 20 mg/mL. Three different patient samples were titrated as described and extracted for intact human IGF-II analysis. The results were compared to the non-spiked pool results and the percent difference was calculated. Data generated for this comparison is presented in Table 21.

TABLE 21

Hemolytic interference studies for intact human IGF-II in patient serum samples
% Recovery Compared to Control

| | Hemoglobin Concentration (mg/mL) | | | | | |
|---|---|---|---|---|---|---|
| | 0 | 2.5 | 5 | 7.5 | 10 | 20 |
| sample 1 | 100.0 | 99.3 | 104.9 | 94.4 | 102.1 | 92.4 |
| sample 2 | 100.0 | 102.7 | 101.1 | 98.9 | 102.7 | 103.3 |
| sample 3 | 100.0 | 95.8 | 102.7 | 100.6 | 103.0 | 109.5 |

As seen in Table 21, all whole blood spiked samples yielded acceptable results (80%-120% of control value) and demonstrated no dependence between intact human IGF-II detection and hemoglobin concentration. Therefore, samples showing light to moderate hemolysis are acceptable.

The effects of lipemia on intact human IGF-II determination were evaluated by titrating brain lipid extract into patient serum to establish estimated lipid concentrations of 0 mg/mL, 2.5 mg/mL, 5 mg/mL, 7.5 mg/mL, 10 mg/mL, and 20 mg/mL. Three different patient samples were titrated as described and extracted for human IGF-II analysis. The results were compared to the non-spiked pool results and percent difference was calculated. Data generated for this comparison is presented in Table 22.

TABLE 22

Lipemic interference studies for intact human IGF-II in patient serum samples
% Recovery Compared to Control

| | Lipid Concentration (mg/mL) | | | | | |
|---|---|---|---|---|---|---|
| | 0 | 2.5 | 5 | 7.5 | 10 | 20 |
| sample 1 | 100.0 | 102.9 | 107.2 | 112.9 | 112.9 | 107.2 |
| sample 2 | 100.0 | 106.2 | 95.5 | 100.0 | 95.3 | 106.5 |
| sample 3 | 100.0 | 108.0 | 93.0 | 95.1 | 92.0 | 106.6 |

As seen in Table 22, all lipid spiked samples yielded acceptable results (80%-120% of control value) and demonstrated no dependence between intact human IGF-II detection and lipid concentration. Therefore, samples showing light to moderate lipemia are acceptable.

The effects of bilirubin on intact human IGF-II determination were evaluated by titrating bilirubin into patient serum to establish estimated bilirubin concentrations of 0 mg/mL, 0.25 mg/mL, 0.5 mg/mL, 0.75 mg/mL, 1 mg/mL, and 2 mg/mL. Three different patient samples were titrated as described and extracted for intact human IGF-II analysis. The results were compared to the non-spiked pool results and the percent difference was calculated. Data generated for this comparison is presented in Table 23.

TABLE 23

Bilirubin interference studies for intact
human IGF-II in patient serum samples
% Recovery Compared to Control

| | Bilirubin Concentration (mg/mL) | | | | |
|---|---|---|---|---|---|
| | 0 | 0.25 | 0.5 | 0.75 | 1 | 2 |
| sample 1 | 100.0 | 87.0 | 92.1 | 100.9 | 96.8 | 108.3 |
| sample 2 | 100.0 | 84.6 | 93.1 | 81.0 | 87.0 | 90.7 |
| sample 3 | 100.0 | 115.3 | 108.9 | 99.5 | 89.2 | 104.9 |

As seen in Table 23, all bilirubin spiked samples yielded acceptable results (80%-120% of control value) and demonstrated no dependence between intact human IGF-II detection and bilirubin concentration. Therefore, samples showing light to moderate bilirubin are acceptable.

The effects of IGFBP-3 on intact human IGF-II determination were evaluated by titrating recombinant IGFBP-3 into patient serum to establish estimated IGFBP-3 concentrations of 5 mg/L, 10 mg/L, and 20 mg/L. Three different patient samples were titrated as described and extracted for intact human IGF-II analysis within three hours of their preparation. Another set of 15 patient samples were spiked with IGFBP-3 to a final concentration of 5 mg/L and equilibrated for three days at 4° C. before extraction. In both experiments, the results were compared to the non-spiked pool results and the percent difference was calculated. Data generated for these comparisons are presented in Tables 24 and 25, respectively.

TABLE 24

IGFBP-3 interference studies for intact human IGF-II in
patient serum samples (extracted 3 hours after preparation)
% Recovery Compared to Control

| | IGFBP-3 Concentration (mg/L) | | |
|---|---|---|---|
| | 5 | 10 | 20 |
| Sample 1 | 104 | 108 | 107 |
| Sample 2 | 101 | 95 | 102 |
| Sample 3 | 101 | 102 | 102 |

TABLE 25

IGFBP-3 interference studies for intact human IGF-II in patient
serum samples (extracted 3 days after preparation)

| Sample | % Recovery Compared to Control (5 mg/L IGFBP-3) |
|---|---|
| 1 | 102.6 |
| 2 | 111.0 |
| 3 | 117.5 |
| 4 | 105.6 |
| 5 | 91.9 |
| 6 | 87.5 |
| 7 | 111.2 |
| 8 | 105.9 |
| 9 | 99.1 |
| 10 | 111.8 |
| 11 | 104.6 |
| 12 | 95.5 |
| 13 | 99.9 |
| 14 | 87.7 |
| 15 | 99.3 |
| Mean | 102% |

As seen in Tables 24 and 25, all IGFBP-3 spiked samples yielded acceptable results (80%-120% of control value) and demonstrated no dependence between intact human IGF-II detection and IGFBP-3 concentration. Therefore, IGFBP-3 does not appear to interfere with the analysis of intact human IGF-II.

Example 17: IGF-II Sample Type Studies

Ten patient pools were collected in four Vacutainer® types: serum, citrate plasma, heparin plasma, and EDTA plasma. Levels of intact human IGF-II were determined in samples from each sample type. A pairwise analysis of variance (ANOVA) only indicated statistically significant differences between serum and citrate plasma. This indicates that serum, heparin plasma, and EDTA plasma are acceptable sample types. Data from these studies are found in Table 26.

TABLE 26

Effect of Sample Type on IGF-II Quantitation
Intact Human IGF-II (measured value)

| Patient | Serum | EDTA plasma | Heparin Plasma | Citrate Plasma |
|---|---|---|---|---|
| 1 | 497.9 | 469.5 | 490.2 | 432.4 |
| 2 | 790.1 | 783.0 | 726.0 | 726.0 |
| 3 | 593.3 | 584.1 | 681.3 | 650.0 |
| 4 | 791.7 | 723.8 | 714.4 | 591.3 |
| 5 | 631.7 | 603.4 | 754.8 | 623.7 |
| 6 | 756.0 | 708.1 | 744.2 | 717.5 |
| 7 | 642.7 | 598.7 | 648.2 | 612.1 |
| 8 | 652.9 | 606.1 | 658.2 | 599.3 |
| 9 | 585.4 | 557.0 | 551.0 | 523.3 |
| 10 | 840.0 | 875.2 | 862.1 | 721.8 |
| p value (compared to serum) | n/a | $p > 0.05$ | $p > 0.05$ | $p < 0.05$ |

Example 18: Simultaneous Quantitation of IGF-II and IGF-I

Samples from 12 patients were prepared and analyzed with the LC-MS method described above. Intact human IGF-I and IGF-II were quantitated simultaneously for each sample. The results of the simultaneous analysis are presented in Table 27.

TABLE 27

Simultaneous Quantitation of IGF-II and IGF-I

| Patient | IGF-II (ng/mL) | IGF-I (ng/mL) |
|---|---|---|
| 1 | 316 | 371 |
| 2 | 207 | 1107 |
| 3 | 389 | 416 |
| 4 | 495 | 279 |
| 5 | 297 | 836 |
| 6 | 408 | 353 |
| 7 | 301 | 45 |
| 8 | 339 | 227 |
| 9 | 83 | 35 |
| 10 | 339 | 214 |
| 11 | 291 | 731 |
| 12 | 477 | 216 |
| 6 | 408 | 353 |

Figure 15A:
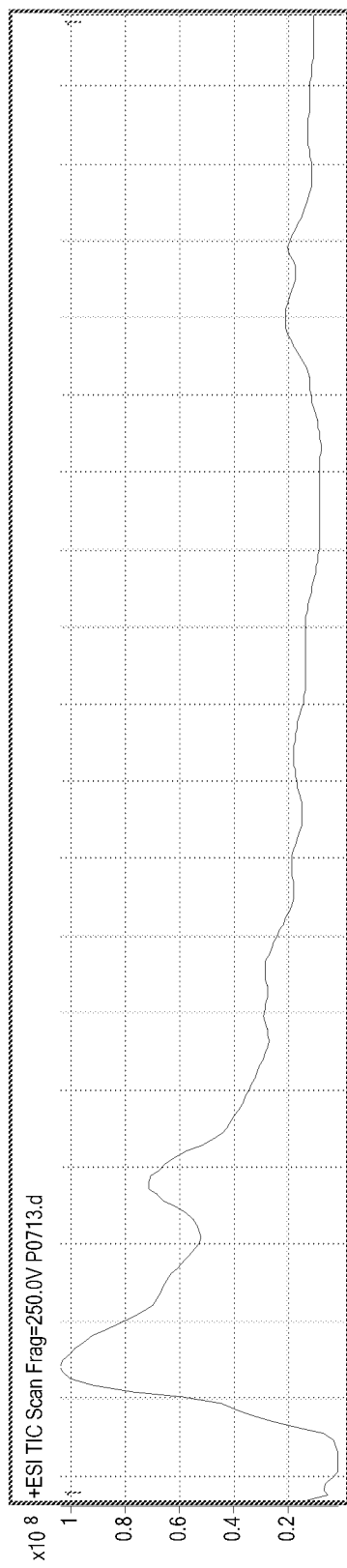
FIGS. 15A, B, and C show an exemplary Total Ion Chromatogram (TIC) and Extracted Ion Chromatograms (EIC) from simultaneous quantitation of IGF-II and IGF-I.
Figure 15B:
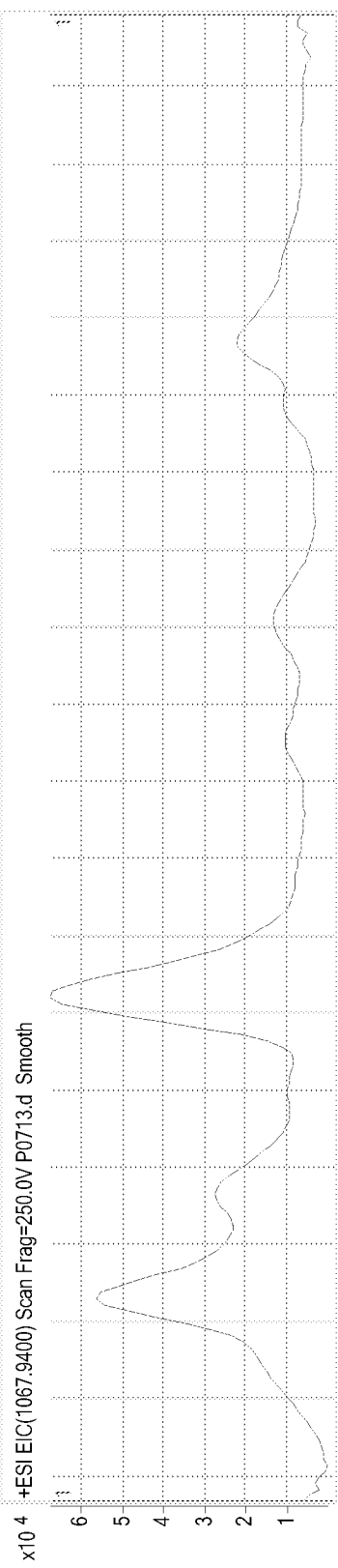
FIG. 15B shows the EIC for IGF-II.
Figure 15C:
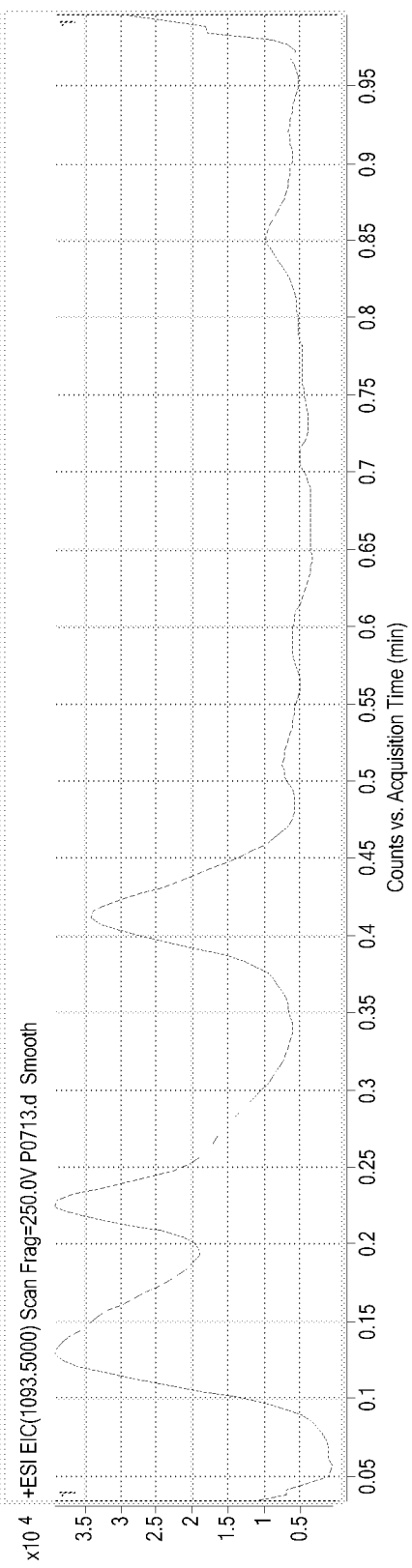
FIG. 15C shows the EIC for IGF-I. Details are discussed in Example 18.

An exemplary Total Ion Chromatogram and Extracted Ion Chromatograms from IGF-II and IGF-I from these studies are shown in FIGS. 15A, 15B, and 15C, respectively.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of an insulin-like growth factor-I (IGF-I) protein in a sample, the method comprising:
   a. ionizing the sample to produce one or more ions detectable by mass spectrometry; and
   b. determining the amount of one or more of the ions comprising an ion with a mass-to-charge ratio of 850.8±2 by high resolution/high accuracy time of flight (TOF) mass spectrometry; and
   c. relating the amount of the determined ion or ions to the amount of IGF-I protein in the sample.

2. The method of claim 1, wherein the method does not include digesting the protein prior to ionization.

3. The method of claim 1, wherein the mass spectrometry is conducted with a mass analyzer capable of a full width at half maximum (FWHM) of greater than or equal to 10,000 and an accuracy of less than or equal to 50 ppm.

4. The method of claim 1, wherein the method comprises determining the amount of an intact long R3 IGF-I.

5. The method of claim 1, further comprising chemically modifying the protein, prior to ionization, to reduce the number of disulfide bridges in the protein.

6. The method of claim 1, further comprising purifying the protein with solid phase extraction (SPE) prior to ionization.

7. The method of claim 1, further comprising purifying the protein by high performance liquid chromatography (HPLC) prior to ionization.

8. The method of claim 1, wherein with the mass analyzer is a time of flight mass analyzer capable of a FWHM of greater than or equal to 20,000 and an accuracy of less than or equal to 10 ppm.

9. The method of claim 1, wherein the sample comprises plasma or serum.

10. The method of claim 1, wherein the one or more ions detectable by mass spectrometry comprise one or more IGF-I ions in a 6+, 7+, 8+, or 9+ charge state.

11. The method of claim 1, wherein the one or more ions used to determine the amount of the IGF-I protein further comprise one or more ions selected from the group of ions with a mass to charge ratio of 1091.9447±0.1, 1092.8031±0.1, 1092.9445±0.1, 1093.0881±0.1, 1093.2308±0.1, 1093.3740±0.1, 1093.5167±0.1, 1093.6597±0.1, 1093.8028±0.1, 1093.9458±0.1, 1094.0889±0.1, 1094.2319±0.1, 1094.3754±0.1, 1094.5185±0.1, 1094.6606±0.1, and 1095.3717±0.1.

* * * * *